US012421327B2

(12) United States Patent
Soula et al.

(10) Patent No.: US 12,421,327 B2
(45) Date of Patent: Sep. 23, 2025

(54) HYDROGELS FOR CELL THERAPY

(71) Applicant: ADOCIA, Lyons (FR)

(72) Inventors: Gérard Soula, Meyzieu (FR);
Alexandre Geissler, Meyzieu (FR);
Nicolas Laurent, Miribel (FR);
Baptiste Plancq, Saint Maurice de Beynost (FR)

(73) Assignee: ADOCIA, Lyons (FR)

( * ) Notice: Subject to any disclaimer, the term of this patent is extended or adjusted under 35 U.S.C. 154(b) by 38 days.

(21) Appl. No.: 17/573,517

(22) Filed: Jan. 11, 2022

(65) Prior Publication Data

US 2022/0220228 A1  Jul. 14, 2022

(30) Foreign Application Priority Data

Jan. 11, 2021 (EP) .................................. 21151038
Dec. 24, 2021 (EP) .................................. 21217754

(51) Int. Cl.
*C08B 37/02* (2006.01)
*A61L 27/20* (2006.01)
*A61L 27/52* (2006.01)

(52) U.S. Cl.
CPC .......... *C08B 37/0021* (2013.01); *A61L 27/20* (2013.01); *A61L 27/52* (2013.01)

(58) Field of Classification Search
CPC .............................. C08B 37/0021; A61L 27/52
See application file for complete search history.

(56) References Cited

U.S. PATENT DOCUMENTS

| | | | |
|---|---|---|---|
| 8,952,095 | B2 | 2/2015 | Wurst et al. |
| 11,873,358 | B2 | 1/2024 | Stewart et al. |
| 2013/0052736 | A1 | 2/2013 | Wurst et al. |
| 2018/0327554 | A1* | 11/2018 | Yoo .......................... A61P 9/06 |
| 2019/0367869 | A1 | 12/2019 | Angres et al. |

FOREIGN PATENT DOCUMENTS

| | | |
|---|---|---|
| EP | 2716662 A1 | 4/2014 |
| EP | 3575391 A1 | 12/2019 |
| EP | 4026853 A1 | 7/2022 |
| WO | 2014/034884 A1 | 3/2014 |
| WO | 2014072035 A1 | 5/2014 |
| WO | 2018218346 A1 | 12/2018 |
| WO | 2019067766 A1 | 4/2019 |
| WO | 2020036918 A1 | 2/2020 |
| WO | 2021/247810 A1 | 12/2021 |
| WO | 2022/148887 A1 | 7/2022 |

OTHER PUBLICATIONS

Daniele et al., Biomaterials, 2014, 35, p. 1845-1856. (Year: 2014).*
Xu et al., Langmuir, 2006, 22, p. 3352-3357. (Year: 2006).*
Song et al., Polymers, 2017, 9(9), article 409, 13 pages. (Year: 2017).*
Mora, Nestor Lopez et al., "Evaluation of Dextran (Ethylene Glycol) Hydrogel Films for Giant Unilamellar Lipid Vesicle Production and Their Application for the Encapsulation of Polymersomes", Soft Matter, (2017), vol. 13, No. 33, pp. 5580-5588.
Zhang, Hanwei et al., "In Situ Gelable Interpenetrating Double Network Hydrogel Formulated From Binary Components: Thiolated Chitosan and Oxidized Dextran", Biomacromolecules (2011), vol. 12, No. 5, pp. 1428-1437.
Zhang, Rhongsheng et al., "A Novel pH- and Ionic-Strength-Sensitive Carboxy Methyl Dextran Hydrogel", Biomaterials, vol. 26, No. 22, (2005), pp. 4677-4683.
Ito, Taichi et al., "Dextran-Based In Situ Cross-Linked Injectable Hydrogels to Prevent Peritoneal Adhesions", Biomaterials, vol. 28, No. 23, (2007), pp. 3418-3426.
Jul. 1, 2021 Extended European Search Report issued in European Application No. 21151038.3.
Xiao Y. et al, "Injectable thermosensitive hydrogel-based drug delivery system for local cancer therapy", Colloids and Surfaces B: Biointerfaces, v. 200, article 111581, Jan. 16, 2021.
Apr. 5, 2022 International Search Report and Written Opinion issued in PCT/EP2022/050466.
Nov. 29, 2022 Written Opinion issued in PCT/EP2022/050466.
Feb. 27, 2023 International Preliminary Report on Patentability issued in PCT/EP2022/050466.
Jan. 13, 2025 International Preliminary Report on Patentability issued in PCT/EP2023/069584.
Jun. 5, 2024 Written Opinion issued in PCT/EP2023/069586.
Jun. 5, 2024 Written Opinion issued in PCT/EP2023/069584.
Jan. 4, 2023 European Search Report issued in European Application 22184567.
Jan. 4, 2023 Euopean Search Opinion issued in European Application 22184567.
Trudel J., "Assessment of cytotoxicity of photocrosslinked dextran and hyaluronan-based hydrogels to vascular smooth muscle cells", Biomaterials, v. 23, p. 3299-3307, 2002.
Oct. 23, 2023 International Search Report issued in PCT/EP 2023/069586.
Oct. 23, 2023 Written Opinion of the International Searching Authority issued in PCT/EP2023/069586.
Oct. 25, 2024 International Preliminary Report on Patentability issued in PCT/EP2023/069586.
Jan. 9, 2023 European Search Report issued in European Application 22184569.
Jan. 9, 2023 European Search Opinion issued in European Application 22184568.
Oct. 16, 2023 Written Opinion issued in PCT/EP2023/069584.
Oct. 16, 2023 International Search Report issued in PCT/EP2023/069584.

(Continued)

*Primary Examiner* — Jonathan S Lau
(74) *Attorney, Agent, or Firm* — Oliff PLC

(57) ABSTRACT

A crosslinked dextran polymer, bearing carboxylate groups, wherein at least two saccharidic units of dextran belonging to two different polymer chains are covalently linked by at least one at least divalent radical, this at least divalent radical being a linear, branched or cyclic alkyl radical including at least 15 carbon atoms and optionally heteroatoms such as oxygen, nitrogen or sulfur.

18 Claims, 1 Drawing Sheet

(56) References Cited

OTHER PUBLICATIONS

Jukes, J.M., "A Newly Developed Chemically Crosslinked Dextran-Poly(Ethylene Glycol) Hydrogel for Cartilage Tissue Engineering", Tissue Eng. Part A, v.16, n.2, p. 565-573, Oct. 23, 2009.

Bauer, M., et al, "Poly(2-ethyl-2-oxazoline) as Alternative for the Stealth Polymer Poly(ethylene glycol): Comparison of in vitro Cytotoxicity and Hemocompatibility", Macromolecular Bioscience, v. 12, p. 986-998, May 30, 2012.

* cited by examiner

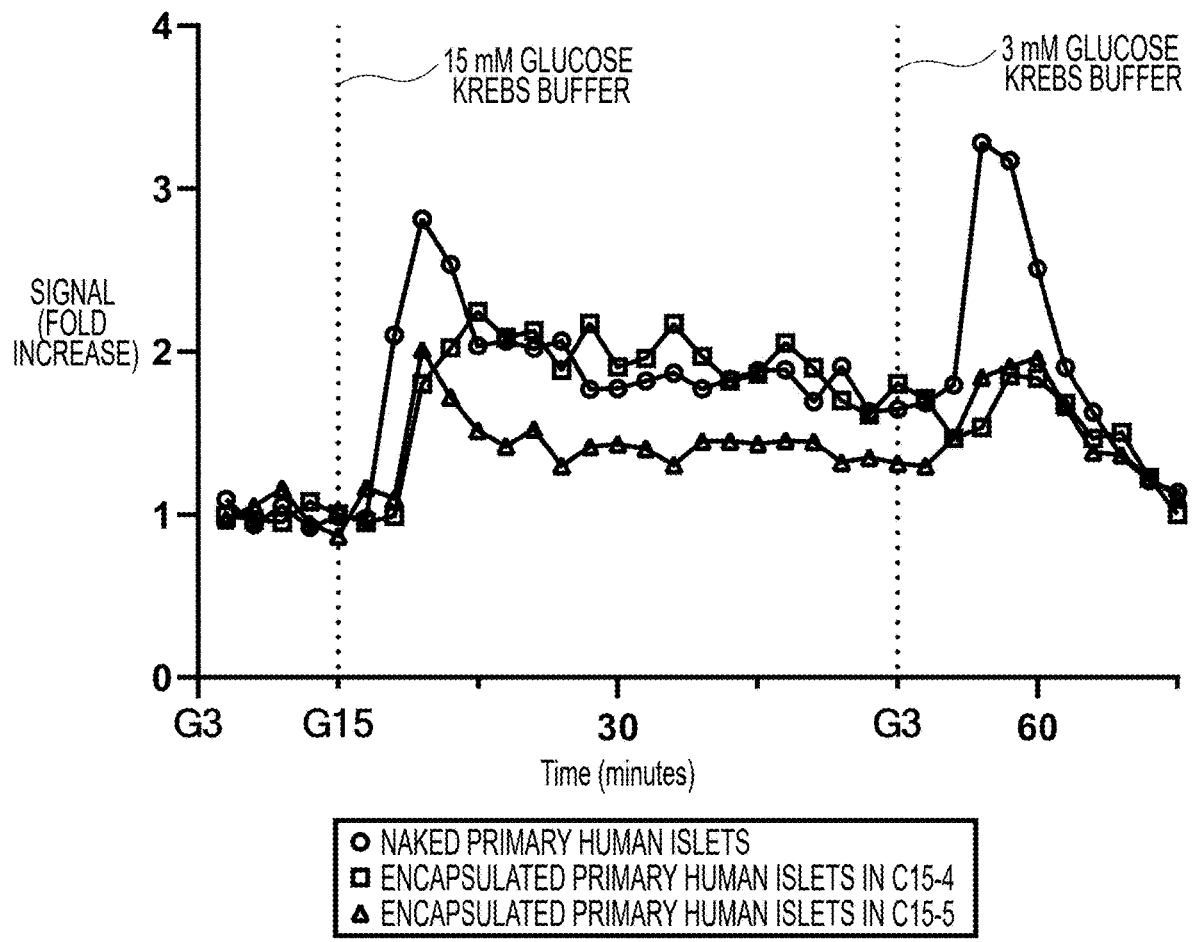

HYDROGELS FOR CELL THERAPY

The domain of the invention is therapy, in particular cell therapy. More particularly the invention is about an implant comprising a hydrogel which may incorporate:
- active principles, such as peptides, hormones or proteins, or
- secreting cells, which may be cells secreting peptides or hormones.

The aim is to prevent, treat or cure disease. In particular, this could allow the prevention and/or treatment of chronic diseases by replacing totally or in part the function of natural occurring cells which are deficient in the patients. The invention is also about a crosslinked polymer, its precursors, a process for obtaining the crosslinked polymer and a process for obtaining a hydrogel, in particular a hydrogel containing cells.

The cells may be isolated or aggregated and may be of one type or of different types.

Hydrogels can be used in multiple systems like:
- scaffolds as controlled drug or active pharmaceutical ingredient release systems or
- scaffolds to be used as implantable device comprising cells.

Hydrogels comprise or consist of polymers that are crosslinked in a 3D network. They can either be natural or synthetic, homopolymers or copolymers. They have the ability to absorb and retain large amounts of water. This is known as the swelling of hydrogels.

In order to have a system which may be an implant able to deliver active principle on the long run, many features have to be obtained.

Among these features may be cited:
- a low degradability, in particular a low biodegradability or a good in vivo stability, in order for the cells not to go in the organism of the patient,
- a good permselectivity, allowing a low, or even better no, immune response by isolating the incorporated cells, totally or in part, from the immune system of the host while allowing the passage of the active principle, for example a hormone, peptide or protein,
- a good mitigation of the foreign body response, or a good biocompatibility, in particular a low cytotoxicity and a good local tolerance,
- allowing the cells to have a high survival rate, such as having a good vascularisation close to the cells,
- allowing the cells to have a good functionality within the hydrogel.

In order to be used as controlled release systems or scaffolds for cells, hydrogels must have particular characteristics so as to exhibit all or part of the desired properties such as disclosed above as well as good mechanical and rheological properties.

Among the rheological and mechanical properties that are of high interest for the hydrogel may be cited:
- a good homogeneity, which can be linked to a good transparency or translucency,
- appropriate resistance and flexibility toward stress and strain mechanics, in particular when being handled and implanted,
- a defined mesh size to maximise oxygen and nutrients exchanges, controlled transport properties and permselectivity
- a good stability in vivo, i.e. resistance to enzymatic or oxidative degradation.

Among parameters which can give indications on the rheological and mechanical desired properties may be cited:
- tan $\delta$ (called loss tangent) which gives indication on mechanical properties,
- G', which gives indication on the mesh size and on the elastic properties,
- compression and/or traction deformation at break, which gives indication on the elasticity and resistance of the hydrogel,
- swellability, which gives indications on mechanical properties.

The following prior art on hydrogel:
- Nestor Loper Mora et al, "evaluation of dextran(ethyleneglycol) hydrogel films for giant unilamellar lipid vesicle production and their application for the encapsulation of polymersome, Soft Matters, January 2017, Vol. 13, no. 33, pp 5580-5585,
- Hanwei Zhang et al., "In situ gelable interpenetrating double network hydrogel formulated from binary components: thiolated chitosan and oxidized dextran", Biomacromolecules, 2011, Vol. 12, no. 5, pp 1428-1437,
- Rongsheng Zhang et al., "A novel pH and ionic strength sensitive carboxymethyl dextran hydrogel, Biomaterials, 2005, Vol. 26, no. 22, pp 4677-4683, and
- Taichi Ito et al., "Dextran-based in situ cross-linked injectable hydrogels to prevent peritoneal adhesions", Biomaterials, 2007, Vol. 28, no. 23, pp 3418-3426, disclose hydrogels which are not able to technical problems as the hydrogels of the invention do.

Comparative examples show the superiority of the hydrogels according to the invention compared with the hydrogels of the above cited prior art.

The underlying problem is solved by the provision of a gel that presents physicochemical properties to allow the manufacture of an implantable device and biocompatibility properties that allow the cells survival.

Moreover, and on the contrary to many prior arts, the invention allows the preparation of hydrogels which have tunable features, considering the precursors used and the way the crosslinking is performed. This can lead to hydrogels having a controlled incorporation and release of specific objects from the hydrogel.

The suitability of the hydrogel depends on its bulk structure, thus important parameters used to characterize the network structure of the hydrogel according to the invention are the polymer volume fraction in the swollen state, the molecular weight of the polymer chain between two neighbouring cross-linking points, and the corresponding mesh size.

The problem is solved by the provision of a new crosslinked dextran polymer, bearing carboxylate groups, wherein at least two saccharidic units of dextran belonging to two different polymer chains are covalently linked by at least one divalent radical, this at least divalent radical being a linear, branched or cyclic alkyl radical comprising at least 15 carbon atoms and optionally heteroatoms such as oxygen, nitrogen or sulfur.

BRIEF DESCRIPTION OF THE DRAWINGS

FIG. 1 is a graph depicting an insulin secretion response to glucose stimulation.

DETAILED DESCRIPTION

FIG. 1 shows the insulin secretion response to glucose stimulation measured in perifusion for naked primary human islets (circle) compared to encapsulated primary human islets in C15-4 (squares) and in C15-5 (triangle). G3 is a 3 mM glucose Krebs buffer/G15 is 25 a 15 mM glucose Krebs buffer. N=1 independent experiment, n=1 sample. The x-axis being the time (in minutes) and the y-axis being the signal (fold increase).

The properties of this family of hydrogels are tunable and tailorisable to the applications by choosing and adapting the cross-linking reaction conditions, the substitution degree and molecular weight of the dextrans and cross-linkers.

In an embodiment, the cross-linked dextran polymer according to the invention is a dextran polymer bearing carboxylate groups wherein the at least divalent radical $L(-)_i$ is covalently bound to the dextran polymer backbone with i —$(R_1)_m G_1$-_radicals, wherein, $L(-)_i$ is a linear or branched polyether bearing at its ends, heteroatoms such as oxygen, nitrogen or sulfur, i is the valence of L and the number of —$(R_1)_m G_1$—_radicals and is an integer comprised from 2 to 8 ($2 \leq i \leq 8$), m is an integer equal to 0 or 1, —$R_1$— is a linear or branched alkyl divalent radical comprising from 1 to 6 carbon atoms and optionally heteroatoms such as oxygen, nitrogen or sulfur, -$G_1$- is a linear or branched or cyclic alkyl divalent radical comprising from 1 to 6 carbon atoms and may comprise heteroatoms such as oxygen, nitrogen or sulfur.

In an embodiment, when m is 1, —$R_1$— is linked to the dextran and -$G_1$- is linked to the linker.

In an embodiment, the cross-linked dextran polymer according to the invention is a dextran polymer wherein $L(-)_i$ is a linear polyether radical bearing at its ends, at least two heteroatoms such as oxygen, nitrogen or sulfur.

In an embodiment, the cross-linked dextran polymer according to the invention is a dextran polymer wherein $L(-)_i$ is a branched polyether radical bearing at its ends, at least two heteroatoms such as oxygen, nitrogen or sulfur.

By branched polyether is meant several polyether arms connected by a linker. The linker may be an alkyl comprising between 2 to 20 carbon atoms, and optionally heteroatoms such as oxygen, nitrogen or sulfur.

In an embodiment, the cross-linked dextran polymer according to the invention is a dextran polymer wherein $L(-)_i$ is a linear or branched polyether bearing at its ends, at least two heteroatoms such as oxygen, nitrogen or sulfur comprising at most 8 arms.

In an embodiment, the cross-linked dextran polymer according to the invention is a dextran polymer wherein $L(-)_i$ with i=2 is a branched or linear polyether bearing at its ends 2 heteroatoms such as oxygen, nitrogen or sulfur comprising 2 arms.

In an embodiment, the cross-linked dextran polymer according to the invention is a dextran polymer, wherein $L(-)_i$ with i=3 is a branched polyether bearing at its ends, 3 heteroatoms such as oxygen, nitrogen or sulfur comprising 3 arms.

In an embodiment, the cross-linked dextran polymer according to the invention is a dextran polymer, wherein $L(-)_i$ with i=4 is a branched polyether bearing at its ends, 4 heteroatoms such as oxygen, nitrogen or sulfur comprising 4 arms.

In an embodiment, the cross-linked dextran polymer according to the invention is a dextran polymer wherein $L(-)_i$ with i=5 is a branched polyether bearing at its ends, 5 heteroatoms such as oxygen, nitrogen or sulfur comprising 5 arms.

In an embodiment, the cross-linked dextran polymer according to the invention is a dextran polymer wherein $L(-)_i$ with i=6 is a branched polyether bearing at its ends, 6 heteroatoms such as oxygen, nitrogen or sulfur comprising 6 arms.

In an embodiment, the cross-linked dextran polymer according to the invention is a dextran polymer wherein $L(-)_i$ with i=7 is a branched polyether bearing at its ends, 7 heteroatoms such as oxygen, nitrogen or sulfur comprising 7 arms.

In an embodiment, the cross-linked dextran polymer according to the invention is a dextran polymer wherein $L(-)_i$ with i=8 is a branched polyether bearing at its ends, 8 heteroatoms such as oxygen, nitrogen or sulfur comprising 8 arms.

In an embodiment, the cross-linked dextran polymer according to the invention is a dextran polymer wherein $L(-)_i$ with i=2 is a linear polyether bearing at its ends 2 sulfur atoms.

In an embodiment, the cross-linked dextran polymer according to the invention is a dextran polymer wherein $L(-)_i$ with i=4 is a branched polyether bearing at its ends at most 4 sulfur atoms.

In an embodiment, the cross-linked dextran polymer according to the invention is a dextran polymer wherein $L(-)_i$ is a branched polyether bearing at its ends a sulfur atom and comprising at most 8 arms.

In an embodiment, the cross-linked dextran polymer according to the invention is a dextran polymer wherein $L(-)_i$ is a branched polyether bearing at its ends 2 sulfur atoms and comprising 2 arms.

In an embodiment, the cross-linked dextran polymer according to the invention is a dextran polymer wherein $L(-)_i$ with i=3 is a branched polyether bearing at its ends 3 sulfur atoms and comprising 3 arms.

In an embodiment, the cross-linked dextran polymer according to the invention is a dextran polymer wherein $L(-)_i$ with i=4 is a branched polyether bearing at its ends 4 sulfur atoms and comprising 4 arms.

In an embodiment, the cross-linked dextran polymer according to the invention is a dextran polymer wherein $L(-)_i$ with i=8 is a branched polyether bearing at its ends 8 sulfur atoms and comprising 8 arms.

In an embodiment, the cross-linked dextran polymer according to the invention is a dextran polymer wherein $L(-)_i$ is a radical issued from a linear or branched mercaptopolyethyleneglycol comprising at least 2 sulfur atoms and comprising at most 8 arms, which number-average molecular weight (Mn) is comprised from 500 to 40 000 g/mol ($500 \leq Mn \leq 40\ 000$ g/mol) or polymerisation degree (DP) is comprised from 8 to 1000 ($8 \leq DP \leq 1000$).

In an embodiment, the cross-linked dextran polymer according to the invention is a dextran polymer wherein $L(-)_i$ is a radical issued from a linear or branched mercaptopolyethyleneglycol comprising at least 2 sulfur atoms and comprising at most 8 arms, which Mn is comprised from 1000 to 25 000 g/mol ($1000 \leq Mn \leq 25\ 000$ g/mol) or polymerisation degree (DP) is comprised from 15 to 600 ($15 \leq DP \leq 600$).

In an embodiment, the cross-linked dextran polymer according to the invention is a dextran polymer wherein $L(-)_i$ is a radical issued from a mercaptopolyethyleneglycol according to formula II:

$$—S—(CH_2—CH_2—O)_p—CH_2—CH_2—S—$$ Formula II wherein p is an integer comprised from 8 to 1000 ($8 \leq p \leq 1000$).

In an embodiment, the cross-linked dextran polymer according to the invention is a dextran polymer wherein $L(-)_i$ is a radical according to formula III' issued from a mercaptoethyl polyoxyethylene:

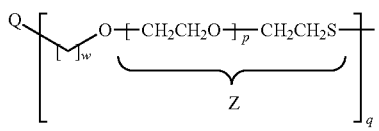

Formula III' wherein
- Q is either a carbon atom or an alkyl chain comprising 2 to 10 carbon atoms, the alkyl chain may comprise heteroatom chosen from the group consisting of oxygen, sulfur and nitrogen
- p is an integer comprised from 8 to 1000 ($8 \leq p \leq 1000$)
- q is an integer comprised from 2 to 8 ($2 \leq q \leq 8$)
- w is 1 or 2, and
- Z is $-(CH_2-CH_2O)_p-CH_2-CH_2-S-$.

In an embodiment, w is 1.

In an embodiment, the crosslinked dextran polymer according to the invention is a dextran polymer wherein $L(-)_i$ is a radical according to formula III issued from a mercaptoethyl polyoxyethylene:

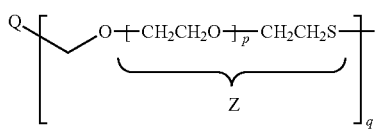

Formula III wherein
- Q is either a carbon atom or an alkyl chain comprising from 2 to 10 carbon atoms, the alkyl chain may comprise heteroatom chosen from the group consisting of oxygen, sulfur and nitrogen
- p is an integer comprised from 8 to 1000 ($8 \leq p \leq 1000$)
- q is an integer comprised from 2 to 8 ($2 \leq q \leq 8$)
- Z is $-(CH_2-CH_2O)_p-CH_2-CH_2-S-$.

In an embodiment Q is an alkyl chain comprising from 2 to 8 carbon atoms and 1 or 2 oxygen atoms.

In an embodiment, the cross-linked dextran polymer according to the invention is a dextran polymer wherein $L(-)_i$ corresponding to Formula III' with q=4 and Q is a carbon atom, and is a radical according to formula VII

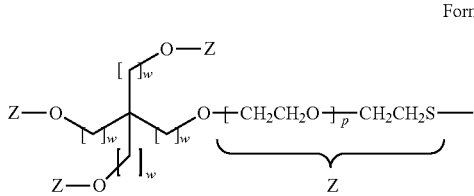

Formula VII wherein
- Z is $-(CH_2-CH_2O)_p-CH_2-CH_2-S-$
- p is comprised from 8 to 1000 ($8 \leq p \leq 1000$)
- w is comprised from 1 to 2, ($1 \leq w \leq 2$).

In an embodiment, w is 1.

In an embodiment, the crosslinked dextran polymer according to the invention is a dextran polymer wherein $L(-)_i$ is a radical according to formula VII'

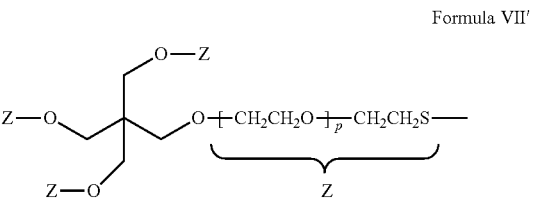

Formula VII'

Wherein:
- p is comprised from 8 to 1000, ($8 \leq p \leq 1000$) and
- Z is $-(CH_2-CH_2O)_p-CH_2-CH_2-S-$.

In an embodiment, the cross-linked dextran polymer according to the invention is a dextran polymer wherein $L(-)_i$ is a radical according to formula II, III, III', VII or VII' issued from the thiol polyethylene glycols or mercaptopolyoxyethylenes cited in the following table:

| Chemical Name | i | Mn (kg/mol) |
|---|---|---|
| Poly(ethylene glycol) dithiol | 2 | 10 |
| Poly(ethylene glycol) dithiol | 2 | 3.4 |
| Poly(ethylene glycol) dithiol | 2 | 1 |
| Pentaerythritol tetra(mercaptoethyl) polyoxyethylene | 4 | 5.2 |
| Pentaerythritol tetra(mercaptoethyl) polyoxyethylene | 4 | 20 |
| tripentaerythritol octa(mercaptoethyl) polyoxyethylene | 8 | 20 |

In an embodiment, the cross-linked dextran polymer according to the invention is a dextran polymer wherein $L(-)_i$ is a radical according to formula VII with w=1 or formula VII' in particular issued from a pentaerythritol tetra(mercaptoethyl) polyoxyethylene, CAS #188492-68-4.

In an embodiment, the cross-linked dextran polymer according to the invention is a dextran polymer wherein $-R_1-$ is a linear or branched alkyl divalent radical comprising from 1 to 6 carbon atoms and optionally heteroatoms such as oxygen, nitrogen or sulfur.

In an embodiment, the cross-linked dextran polymer according to the invention is a dextran polymer wherein $-R_1-$ is a linear or branched alkyl divalent radical comprising a nitrogen atom.

In an embodiment, the cross-linked dextran polymer according to the invention is a dextran polymer wherein $-R_1-$, is a linear alkyl radical comprising from 1 to 6 carbon atoms and a nitrogen atom.

In an embodiment, the cross-linked dextran polymer according to the invention is a dextran polymer wherein $-R_1-$, is a linear alkyl radical comprising from 2 to 5 carbon atoms and a nitrogen atom.

In an embodiment, the cross-linked dextran polymer according to the invention is a dextran polymer wherein $-R_1-$, is a linear alkyl radical comprising from 3 to 4 carbon atoms and a nitrogen atom.

In an embodiment, the cross-linked dextran polymer according to the invention is a dextran polymer wherein $-R_1-$, is a linear alkyl radical comprising 2 carbon atoms and a nitrogen atom.

In an embodiment, the cross-linked dextran polymer according to the invention is a dextran polymer wherein —$R_1$—, is a linear alkyl radical comprising from 2 to 5 carbon atoms and a nitrogen atom according to formula XIII:

Formula XIII

In an embodiment, the cross-linked dextran polymer according to the invention is a dextran polymer wherein radical —$R_1$— is covalently bound by an amide function resulting of the reaction of a carboxylate group borne by the dextran with one —$R_1$— precursor or —$(R_1)_mG_1$- precursor bearing an amine function.

In an embodiment, the cross-linked dextran polymer according to the invention is a dextran polymer wherein radical —$R_1$— is covalently bound by an ether function resulting of the reaction of the hydroxyl function borne by the dextran with one —$R_1$— precursor or —$(R_1)_mG_1$- precursor bearing a leaving group, in particular a halogen atom.

In an embodiment, the cross-linked dextran polymer according to the invention is a dextran polymer wherein the radical -$G_1$- is a divalent radical according to formula V:

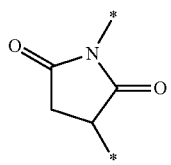

Formula V wherein the -* represent the attachment sites to the dextran backbone and to the linker.

In an embodiment, the cross-linked dextran polymer according to the invention is a dextran polymer wherein the radical -$G_1$- is a radical according to formula V':

Formula V'

In an embodiment, the cross-linked dextran polymer according to the invention is a dextran polymer wherein —$(R_1)_mG_1$- covalently bound to a carboxylate group borne by the dextran polymer backbone is a divalent radical according to formula VI:

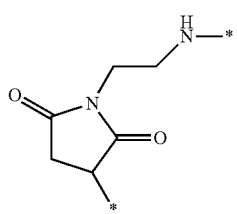

Formula VI wherein the -* represent the attachment sites to the dextran backbone and to the linker.

In an embodiment, the cross-linked dextran polymer according to the invention is a dextran polymer wherein —$(R_1)_mG_1$- covalently bound to a carboxylate group borne by the dextran polymer backbone is a divalent radical according to formula VIII:

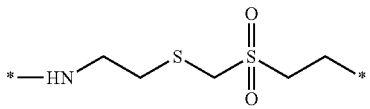

Formula VIII wherein the -* represent the attachment sites to the dextran backbone and to the linker.

In an embodiment, the cross-linked dextran polymer according to the invention is a dextran polymer wherein —$(R_1)_mG_1$- covalently bound to a hydroxyl function borne by the dextran polymer backbone is a divalent radical according to formula X:

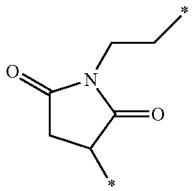

Formula X wherein the -* represent the attachment sites to the dextran backbone and to the linker.

In an embodiment, the cross-linked dextran polymer according to the invention is a dextran polymer wherein —$(R_1)_mG_1$- covalently bound to a hydroxyl function borne by the dextran polymer backbone is a divalent radical according to formula XI:

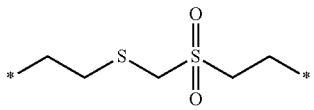

Formula XI wherein the -* represent the attachment sites to the dextran backbone and to the linker.

In an embodiment in Formulas VI and X, —$(R_1)_mG_1$- is linked to the dextran via the upper bond ie via —$R_1$— or N-ethyl bond and to the linker via the lower bond, ie the bond from the saturated ring.

In an embodiment in Formulas VIII and XI, —$(R_1)_mG_1$- is linked to the dextran via the left bond ie via —$R_1$— and to the linker via the right bond.

In an embodiment, the cross-linked dextran polymer according to the invention is a dextran polymer wherein the carboxylate groups bound to the saccharidic units are bound by ether bonds and chosen amongst linear or branched alkyl radicals bearing at least a carboxylate group.

In an embodiment, the cross-linked dextran polymer according to the invention is a dextran polymer wherein carboxylate groups bound to the saccharidic units are bound by ether bonds and chosen amongst carboxylate groups according to formula I

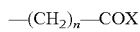

Formula I wherein
  n is an integer comprised from 1 to 7 ($1 \leq n \leq 7$)
  X is chosen amongst —OH, —ONa, —OK or —$(R_1)_mG_1$- radical.

In an embodiment, the cross-linked dextran polymer according to the invention is a dextran polymer wherein carboxylate groups according to formula I —$(CH_2)_n$—COX are covalently bound to the dextran polymer backbone by an ether function resulting of the reaction of the hydroxyl function borne by the dextran with one —$(CH_2)_n$—COX precursor bearing a leaving group, in particular a halogen atom.

In an embodiment, the cross-linked dextran polymer according to the invention is a dextran polymer wherein —$(CH_2)_n$—COX which is not bound to —$(R_1)_mG_1$- radical is in a salt form and X is chosen amongst ONa or OK.

In an embodiment, the cross-linked dextran polymer according to the invention is a dextran polymer bearing carboxylate groups according to formula I wherein n is comprised from 1 to 7.

In an embodiment, the cross-linked dextran polymer according to the invention is a dextran polymer bearing carboxylate groups according to formula I wherein n is comprised from 1 to 6.

In an embodiment, the cross-linked dextran polymer according to the invention is a dextran polymer bearing carboxylate groups according to formula I wherein n is comprised from 1 to 5.

In an embodiment, the cross-linked dextran polymer according to the invention is a dextran polymer bearing carboxylate groups according to formula I wherein n is comprised from 1 to 4.

In an embodiment, the cross-linked dextran polymer according to the invention is a dextran polymer bearing carboxylate groups according to formula I wherein n is comprised from 1 to 3.

In an embodiment, the cross-linked dextran polymer according to the invention is a dextran polymer bearing carboxylate groups according to formula I wherein n is comprised from 1 to 2.

In an embodiment, the cross-linked dextran polymer according to the invention is a dextran polymer bearing carboxylate groups according to formula I wherein n is 1.

In an embodiment, the cross-linked dextran polymer according to the invention is a dextran polymer wherein the dextran polymer backbone is according to formula XII,

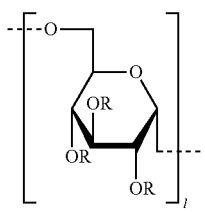

Formula XII wherein R is chosen among
—H, —$(CH_2)_n$—COX or —$(R_1)_mG_1$-; n, m, X, —$R_1$—, -$G_1$- and L(–)$_i$ being defined as above and L(–)$_i$ being covalently bound to another dextran polymer backbone with a —$(R_1)_mG_1$- radical, and
I is comprised from 20 to 5000 (20≤I≤5000)

In an embodiment, the cross-linked dextran polymer according to the invention is a dextran polymer wherein the dextran polymer backbone is a dextran having a weight average molecular weight (Mw) comprised from 5 to 1000 kDa before cross-linking and substitution.

In other words, the cross-linked dextran polymer according to the invention is obtained after substitution and cross-linking of a native dextran polymer having a weight average molecular weight (Mw) comprised from 5 to 1000 kDa.

In an embodiment, the cross-linked dextran polymer according to the invention is a dextran polymer wherein the dextran polymer backbone is a dextran having a weight average molecular weight (Mw) comprised from 5 to 250 kDa before cross-linking and substitution.

In an embodiment, the cross-linked dextran polymer according to the invention is a dextran polymer wherein the dextran polymer backbone is a dextran having a weight average molecular weight (Mw) comprised from 5 to 100 kDa before cross-linking and substitution.

In an embodiment, the cross-linked dextran polymer according to the invention is a dextran polymer wherein the dextran polymer backbone is a dextran having a weight average molecular weight (Mw) comprised from 5 to 50 kDa before cross-linking and substitution.

In an embodiment, the cross-linked dextran polymer according to the invention is a dextran polymer wherein the dextran polymer backbone is a dextran having a weight average molecular weight (Mw) comprised from 5 to 25 kDa before cross-linking and substitution.

In an embodiment, the cross-linked dextran polymer according to the invention is a dextran polymer wherein the dextran polymer backbone is a dextran having a weight average molecular weight (Mw) comprised from 250 to 1000 kDa before cross-linking and substitution.

In an embodiment, the cross-linked dextran polymer according to the invention is a dextran polymer wherein the dextran polymer backbone is a dextran having a weight average molecular weight (Mw) comprised from 10 to 500 kDa before cross-linking and substitution.

In an embodiment, the cross-linked dextran polymer according to the invention is a dextran polymer wherein the dextran polymer backbone is a dextran having a weight average molecular weight (Mw) comprised from 20 to 500 kDa before cross-linking and substitution.

In an embodiment, the cross-linked dextran polymer according to the invention is a dextran polymer wherein the dextran polymer backbone is a dextran having a weight average molecular weight (Mw) comprised from 20 to 100 kDa before cross-linking and substitution.

In an embodiment, the cross-linked dextran polymer according to the invention is a dextran polymer wherein the dextran polymer backbone is a dextran having a weight average molecular weight (Mw) comprised from 20 to 50 kDa before cross-linking and substitution.

In an embodiment, the cross-linked dextran polymer according to the invention is a dextran polymer wherein the dextran polymer backbone is a dextran having a weight average molecular weight (Mw) comprised from 40 to 250 kDa before cross-linking and substitution.

In an embodiment, the cross-linked dextran polymer according to the invention is a dextran polymer wherein the dextran polymer backbone is a dextran having a weight average molecular weight (Mw) comprised from 40 to 100 kDa before cross-linking and substitution.

In an embodiment, the cross-linked dextran polymer according to the invention is a cross-linked dextran polymer wherein the degree of substitution ($DS_1$) of the dextran backbone with the —$(R_1)_mG_1$- groups is comprised in the range from 0.001 to 0.4 (0.001≤$DS_1$≤4).

In an embodiment, the cross-linked dextran polymer according to the invention is a cross-linked dextran polymer wherein the degree of substitution ($DS_1$) of the dextran backbone with the —$(R_1)_mG_1$- groups is comprised in the range from 0.01 to 0.4 (0.01≤$DS_1$≤0.4).

In an embodiment, the cross-linked dextran polymer according to the invention is a cross-linked dextran polymer wherein the degree of substitution ($DS_1$) of the dextran backbone with the $—(R_1)_mG_1-$ groups is comprised in the range from 0.1 to 0.4 ($0.1 \leq DS_1 \leq 0.4$).

In an embodiment, the cross-linked dextran polymer according to the invention is a cross-linked dextran polymer wherein the dextran polymer backbone is a dextran having a weight average molecular weight (Mw) is from 5 to 250 kDa before cross-linking and substitution and the degree of substitution ($DS_1$) of the dextran backbone with the $—(R_1)_mG_1-$ groups is comprised in the range from 0.1 to 0.4 ($0.1 \leq DS_1 \leq 0.4$).

In an embodiment, the cross-linked dextran polymer according to the invention is a cross-linked dextran polymer wherein the dextran polymer backbone is a dextran having a weight average molecular weight (Mw) is from 20 to 100 kDa before cross-linking and substitution and the degree of substitution ($DS_1$) of the dextran backbone with the $—(R_1)_mG_1-$ groups is comprised in the range from 0.2 to 0.4 ($0.2 \leq DS_1 \leq 0.4$).

In an embodiment, the cross-linked dextran polymer according to the invention is a cross-linked dextran polymer wherein the dextran polymer backbone is a dextran having a weight average molecular weight (Mw) from 20 to 100 kDa before cross-linking and substitution and the degree of substitution ($DS_1$) of the dextran backbone with the $—(R_1)_mG_1-$ groups is comprised in the range from 0.2 to 0.3 ($0.2 \leq DS_1 \leq 0.3$).

In an embodiment, the cross-linked dextran polymer according to the invention is a cross-linked dextran polymer wherein the dextran polymer backbone is a dextran having a weight average molecular weight (Mw) is from 250 to 1000 kDa before cross-linking and substitution and the degree of substitution ($DS_1$) of the dextran backbone with the $—(R_1)_mG_1-$ groups is comprised in the range from 0.001 to 0.4 ($0.001 \leq DS_1 \leq 0.4$).

In an embodiment, the cross-linked dextran polymer according to the invention is a cross-linked dextran polymer wherein the dextran polymer backbone is a dextran having a weight average molecular weight (Mw) from 250 to 1000 kDa before cross-linking and substitution and the degree of substitution ($DS_1$) of the dextran backbone with the $—(R_1)_mG_1-$ groups is comprised in the range from 0.01 to 0.4 ($0.01 \leq DS_1 \leq 0.4$).

In an embodiment, the cross-linked dextran polymer according to the invention is a cross-linked dextran polymer wherein the dextran polymer backbone is a dextran having a weight average molecular weight (Mw) from 250 to 1000 kDa before cross-linking and substitution and the degree of substitution ($DS_1$) of the dextran backbone with the $—(R_1)_mG_1-$ groups is comprised in the range from 0.1 to 0.4 ($0.1 \leq DS_1 \leq 0.4$).

In an embodiment, the cross-linked dextran polymer according to the invention is a cross-linked dextran polymer wherein the degree of substitution ($DS_2$) of the dextran backbone with the carboxylate groups according to formula I is comprised in the range from 0.5 to 3 ($0.5 \leq DS_2 \leq 3$).

In an embodiment, the cross-linked dextran polymer according to the invention is a cross-linked dextran polymer wherein the degree of substitution ($DS_2$) of the dextran backbone with the carboxylate groups according to formula I is comprised in the range from 1 to 2.75 ($1 \leq DS_2 \leq 2.75$).

In an embodiment, the cross-linked dextran polymer according to the invention is a cross-linked dextran polymer wherein the degree of substitution ($DS_2$) of the dextran backbone with the carboxylate groups according to formula I is comprised in the range from 1.5 to 2.5 ($1.5 \leq DS_2 \leq 2.5$).

In an embodiment, the cross-linked dextran polymer according to the invention is a cross-linked dextran polymer wherein the degree of substitution ($DS_2$) of the dextran backbone with the carboxylate groups according to formula I is comprised in the range from 1.75 to 2.25 ($1.75 \leq DS_2 \leq 2.25$).

In an embodiment, the cross-linked dextran polymer according to the invention is a cross-linked dextran polymer having a molar ratio (DC) between the molar concentration of the $—(R_1)_mG_1-$ radical and the molar concentration of the reactive functions of the cross-linker $L(-)_i$ comprised in a range from 0.5 to 1.5 ($0.5 \leq DC \leq 1.5$).

In an embodiment, the cross-linked dextran polymer according to the invention is a cross-linked dextran polymer having a molar ratio between the molar concentration of the $—(R_1)_mG_1-$ radical and the molar concentration of the reactive functions of the cross-linker $L(-)_i$ is comprised in a range from 0.8 to 1.2 ($0.8 \leq DC \leq 1.2$).

In an embodiment, the cross-linked dextran polymer according to the invention is a cross-linked dextran polymer having a molar ratio between the molar concentration of the $—(R_1)_mG_1-$ radical and the molar concentration of the reactive functions of the cross-linker $L(-)_i$ is comprised in a range from 0.9 to 1.1 ($0.9 \leq DC \leq 1.1$)

In an embodiment, the cross-linked dextran polymer according to the invention is a cross-linked dextran polymer having a molar ratio between the molar concentration of the $—(R_1)_mG_1-$ radical and the molar concentration of the reactive functions of the cross-linker $L(-)_i$ is comprised in a range from 0.95 to 1.05 ($0.95 \leq DC \leq 1.05$).

In an embodiment, the cross-linked dextran polymer according to the invention is a cross-linked dextran polymer having a molar ratio between the molar concentration of the $—(R_1)_mG_1-$ radical and the molar concentration of the reactive functions of the cross-linker $L(-)_i$ is 1 (DC=1).

The invention also concerns a hydrogel comprising the cross-linked dextran polymer according to the invention.

In an embodiment the hydrogel is transparent.

By "transparent" is meant that in conditions disclosed in Example C21 for visual inspection an observer considered the sample transparent compared to the standard 2 (6 NTU) and/or the UV absorbance of the hydrogel as measured in Example C21 is lower than 0.06 (Absorbance Units).

In an embodiment the hydrogel is visually transparent and has a UV absorbance <0.06 (Abs. Units).

In an embodiment the hydrogel according to the invention is characterized in that Tan δ is lower than 1.

In the present specification, tan δ is the ratio of the storage modulus (also called elastic modulus) G' to the loss modulus G" (tan δ=G'/G").

In an embodiment the hydrogel according to the invention is characterized in that Tan δ is less than or equal to 0.5.

In an embodiment the hydrogel according to the invention is characterized in that Tan δ is less than or equal to 0.1.

In an embodiment the hydrogel according to the invention is characterized in that Tan δ is less than or equal to 0.05.

In an embodiment the hydrogel according to the invention is characterized in that Tan δ is less than or equal to 0.01.

In an embodiment the hydrogel according to the invention is characterized in that after swelling in water the cross-linked dextran polymer concentration is comprised from 0.01 to 0.2 g/g.

In an embodiment the hydrogel according to the invention is characterized in that after swelling in water the cross-linked dextran polymer concentration is comprised from 0.03 to 0.1 g/g.

In an embodiment the hydrogel according to the invention is characterized in that after swelling in water the cross-linked dextran polymer concentration is comprised from 0.05 to 0.1 g/g.

In an embodiment, the hydrogel is translucid.

In another embodiment the hydrogel is transparent.

In an embodiment, the hydrogel has a Young modulus comprised between 1 to 200 kPa.

In an embodiment, the hydrogel has a Young modulus comprised between 5 to 200 kPa.

In an embodiment, the hydrogel has a Young modulus comprised between 20 to 200 kPa.

In an embodiment, the hydrogel has a Young modulus comprised between 30 to 200 kPa.

In an embodiment, the hydrogel has a Young modulus comprised between 50 to 200 kPa.

In an embodiment, the hydrogel has a Young modulus comprised between 30 to 180 kPa.

In an embodiment, the hydrogel has a Young modulus comprised between 50 to 150 kPa.

In an embodiment, the hydrogel has a G' comprised from 0.5 to 70 kPa.

In an embodiment the hydrogel has a compression deformation at break of more than or equal to 10%.

In an embodiment the hydrogel has a compression deformation at break of more than or equal to 15%.

In an embodiment the hydrogel has a compression deformation at break of more than or equal to 20%.

In an embodiment the hydrogel has a compression deformation at break of more than or equal to 25%.

In an embodiment the hydrogel has a compression deformation at break of more than or equal to 30%.

In an embodiment the hydrogel has a compression deformation at break of more than or equal to 35%.

In an embodiment the hydrogel has a compression deformation at break of more than or equal to 40%.

In an embodiment the hydrogel has a compression deformation at break of more than or equal to 45%.

In an embodiment the hydrogel has a compression deformation at break of more than or equal to 50%.

In an embodiment the hydrogel has a compression deformation at break of more than or equal to 55%.

In an embodiment the hydrogel has a compression deformation at break of more than or equal to 60%.

In an embodiment the hydrogel has a traction deformation at break of more than or equal to 10%.

In an embodiment the hydrogel has a traction deformation at break of more than or equal to 15%.

In an embodiment the hydrogel has a traction deformation at break of more than or equal to 20%.

In an embodiment the hydrogel has a traction deformation at break of more than or equal to 25%.

In an embodiment the hydrogel has a traction deformation at break of more than or equal to 30%.

In an embodiment the hydrogel has a traction deformation at break of more than or equal to 35%.

In an embodiment the hydrogel has a traction deformation at break of more than or equal to 40%.

In an embodiment the hydrogel has a swelling ratio of more than 1.

In an embodiment the hydrogel has a swelling ratio of more than 1.1.

In an embodiment the hydrogel has a swelling ratio of more than or equal to 1.2.

In an embodiment the hydrogel has a swelling ratio of more than or equal to 1.3.

In an embodiment the hydrogel has a swelling ratio of more than or equal to 1.4.

In an embodiment the hydrogel has a swelling ratio of more than or equal to 1.5.

In an embodiment the hydrogel has a swelling ratio of more than or equal to 1.6.

In an embodiment the hydrogel has a swelling ratio of less than or equal to 5.

In an embodiment the hydrogel has a swelling ratio of less than or equal to 4.

In an embodiment the hydrogel has a swelling ratio of less than or equal to 3.

In an embodiment the hydrogel has a swelling ratio of less than or equal to 2.8.

In an embodiment the hydrogel has a water content of at least 80 wt %.

In an embodiment the hydrogel has a water content of at least 85 wt %.

In an embodiment the hydrogel has a water content of at least 90 wt %.

In an embodiment the hydrogel has a water content of at least 97 wt %.

In an embodiment the hydrogel has a water content of at least 96 wt %.

In an embodiment the hydrogel has a water content of at least 95 wt %.

In an embodiment the hydrogel has a water content of at least 94 wt %.

In an embodiment the hydrogel has a water content of at least 93 wt %.

In an embodiment the hydrogel has a water content of at most 99 wt %.

In an embodiment the hydrogel has a water content of at most 98 wt %.

In an embodiment the hydrogel according to the invention is characterized in that it further comprises biological cells.

In an embodiment the cells are cells from human or animal origin.

In an embodiment the cells are cell lines.

In an embodiment the cells are stem-cells derived.

In an embodiment the stem cells are chosen from embryonic-stem cells, from induced-pluripotent-stem-cells or from mesenchymal-stem-cells.

In an embodiment the cells are primary cells.

In an embodiment the cells are proteins, hormones or peptide secreting cells.

In an embodiment the cells are chosen from:
insulin secreting cells for diabetes treatment
Factor VIII or Factor IX secreting cells for hemophilia treatment and
β-glucocerebrosidase secreting cells for Gaucher disease.

In an embodiment the hydrogel according to the invention is characterized in that insulin secreting cells are chosen into the group of pancreatic cells.

In an embodiment the hydrogel according to the invention is characterized in that insulin secreting cells are Langherans islets.

In an embodiment the hydrogel according to the invention is characterized in that the biological cells are pseudoislets.

The invention also concerns the use of a cross-linked dextran copolymer according to the invention into the form of a hydrogel to prepare a cells composition.

In an embodiment the cells are chosen amongst one or multiple type of cells, either isolated or aggregated, which may secrete active principles.

In an embodiment, the cross-linked dextran polymer according to the invention is a dextran polymer bearing carboxylate groups wherein the at least divalent radical $L(-)_i$ is covalently bound to the dextran polymer backbone with i —$(R_1)_m G_1$-. radicals, wherein i is 2, 4 or 8.

In an embodiment, the cross-linked dextran polymer according to the invention is a dextran polymer bearing carboxylate groups wherein the at least divalent radical $L(-)_i$ is covalently bound to the dextran polymer backbone with i —$(R_1)_m G_1$-. radicals, wherein, i is 2.

In an embodiment, the cross-linked dextran polymer according to the invention is a dextran polymer bearing carboxylate groups wherein the at least divalent radical $L(-)_i$ is covalently bound to the dextran polymer backbone with i —$(R_1)_m G_1$-. radicals, wherein, i is 4.

The invention also concerns the precursor of the cross-linked dextran polymer which is a dextran polymer bearing carboxylate groups covalently bound to —$(R_1)_m G_2$ monovalent radicals wherein -$G_2$ which is the precursor of radical -$G_1$- is a Michael acceptor.

In an embodiment, the precursor is a cross-linked dextran polymer as above defined wherein -$G_2$ is chosen amongst maleimide or vinylsulfone or a group comprising a maleimide or vinylsulfone.

In an embodiment, the precursor is a cross-linked dextran polymer as above defined wherein -$G_2$ is a maleimide.

The invention also concerns a process to synthetize a dextran bearing carboxylate groups and at least one —$(R_1)_m G_2$ substituent wherein -$G_2$, a Michael acceptor, precursor of -$G_1$· is chosen amongst linear or branched or cyclic alkyl monovalent radical comprising from 1 to 6 carbon atoms and may comprise heteroatoms such as oxygen, nitrogen or sulfur, $R_1$ being defined as above, comprising the steps of:
a) preparation of a solution of dextran bearing carboxylate groups,
b) substitution of the hydroxyl of the carboxylate group with —$(R_1)_m G_2$.

In an embodiment, the dextran bearing carboxylate groups and at least one —$(R_1)_m G_2$ substituent according to the invention is a dextran polymer wherein -$G_2$ is chosen amongst maleimide or vinylsulfone or a group comprising a maleimide or a vinylsulfone.

In particular embodiments the dextran bearing carboxylate groups and at least one —$(R_1)_m G_2$ substituent is cross-linked with a precursor of the linker $L(-)_i$.

The cross-linking step is performed by mixing the solution comprising the dextran bearing carboxylate groups and at least one —$(R_1)_m G_2$ substituent and a solution of the precursor of the linker $L(-)_i$.

In an embodiment, the precursor of the linker $L(-)_i$ bears functional group ie —SH groups that react with a —$(R_1)_m G_2$ group that comprises vinylsulfone or maleimide groups in a Michael addition reaction to give the cross-linked dextran polymer of the invention.

In an embodiment, the cross-linking step is performed with solutions that comprise from 1 to 150 mM, preferably from 10 to 100 mM of reactive functions —$(R_1)_m G_2$ of the precursor of the dextran carboxylate.

In an embodiment, the cross-linking step is performed with solutions that comprise from 1 to 150 mM, preferably from 10 to 100 mM of reactive functions of the precursor of the linker $L(-)_i$.

In an embodiment, in the cross-linking step, the solution of the dextran polymer precursor bearing reactive functions —$(R_1)_m G_2$ and the solution of the linker $L(-)_i$ precursor are used in equimolar ratio (1:1).

In an embodiment the ratio between the reactive functions —$(R_1)_m G_2$ and reactive functions of the precursor of $L(-)_i$ is comprised from 0.8 to 1.2.

In an embodiment the ratio between the reactive functions —$(R_1)_m G_2$ and reactive functions of the precursor of $L(-)_i$ is comprised from 0.9 to 1.1.

In an embodiment the ratio between the reactive functions —$(R_1)_m G_2$ and reactive functions of the precursor of $L(-)_i$ is 1.

The cross-linking step is a gelation step that leads to the formation of a hydrogel according to the invention.

The hydrogel formation kinetic is function of the temperature and could be modulated by the reactant's concentrations, pH and temperature.

In an embodiment the time to obtain a hydrogel according to the invention is comprised from 1 minute to 6 hours.

In an embodiment the cross-linking step is carried out for 1 hour.

In an embodiment the temperature of the cross-linking step is comprised from 4° C. to room temperature (20-25° C.) and could vary between the step of mixing and the step of gelation and moulding.

In an embodiment the mixing is performed at 4° C. and the gelation is carried out at room temperature (20-25° C.) for 1 hour.

In an embodiment the mixing is performed at room temperature (20-25° C.).

In an embodiment the mixing is performed at 4° C. or room temperature (20-25° C.) and the gelation is carried out at room temperature (20-25° C.) for 1 hour.

In an embodiment, the gelation is carried out at 37° C.

In an embodiment, after cross-linking or gelation, the hydrogel is swelled in a buffer solution, the pH of the buffer solution is comprised from 5 to 8, preferably from 6 to 8 and more preferably from 6.8 to 7.5.

In an embodiment, the buffer solution is a PBS solution at pH 7.4.

In an embodiment, the buffer solution is a Tris solution at pH 7.4.

In an embodiment, the buffer solution is a Tris solution at pH 8.

In an embodiment the swelling allows the hydrogel mass being increased by 1, 2, 3 or 4 compared to its initial mass.

The invention also concerns a process to synthetize a cross-linked dextran polymer according to the invention, into the form of a hydrogel, comprising the steps of:
a) preparation of a sterile solution comprising a dextran bearing methyl carboxylate groups according to formula I and at least two —$(R_1)_m G_2$ radicals,
b) preparation of a sterile solution of mercaptopolyethyleneglycol or mercaptoethyl polyoxyethylene according to formula II, III, III', VII or VII'
c) addition of the sterile solution obtained from step b to the solution obtained from step a,
d) the addition being directly done in a mould or the solutions are introduced into a mould after being mixed,
e) cross-linking and gelation by Michael reaction, for example at room temperature (20-25° C.) or at 37° C., f) unmoulding and swelling to obtain an hydrogel.

In an embodiment steps c) and d) are done simultaneously.

In an embodiment, the swelling is done into a PBS solution at pH 7.4.

In an embodiment of the process according to the invention an active pharmaceutical ingredient (API) is entrapped into the hydrogel.

The invention also concerns a therapeutic use of the hydrogel according to the invention as a therapeutic implant to administer the API to a mammal.

The invention also concerns a process to prepare a hydrogel comprising biological cells comprising the steps of:
- a) preparation of a sterile solution comprising a dextran bearing carboxylate groups according to formula I and at least two —$(R_1)_m G_2$ radicals,
- b) preparation of a sterile solution of mercaptopolyethyleneglycol or mercaptoethyl polyoxyethylene according to formula II, III, III', VII or VII',
- c) preparation of a suspension of biological cells,
- d) mixing the biological cells suspension obtained from step c and the solution obtained from the step b or a,
- e) addition of the sterile solution obtained from step a or b which is not used in step d to the solution obtained from step d,
- f) the addition of step e being either done directly in a mould or the solutions are introduced into a mould after being mixed,
- g) cross-linking and gelation by Michael reaction at room temperature (20-25° C.),
- h) unmoulding and swelling to obtain an hydrogel comprising biological cells.

In an embodiment, the swelling is done into a PBS solution at pH 7.4.

In an embodiment the hydrogel according to the invention is characterized in that it further comprises biological cells.

In an embodiment the cells are cells from human or animal origin.

In an embodiment the cells are cell lines.

In an embodiment the cells are stem-cells derived.

In an embodiment the stem cells are chosen from embryonic-stem cells, from induced-pluripotent-stem-cells or from mesenchymal-stem-cells.

In an embodiment the cells are primary cells.

In an embodiment the cells are protein(s), hormone(s) or peptide(s) secreting cells.

In an embodiment the cells are chosen from
insulin secreting cells for diabetes treatment
Factor VIII or Factor IX secreting cells for hemophilia treatment and
β-glucocerebrosidase secreting cells for Gaucher disease.

In an embodiment the hydrogel according to the invention is characterized in that insulin secreting cells are chosen into the group of pancreatic cells.

In an embodiment the hydrogel according to the invention is characterized in that insulin secreting cells are Langherans islets.

In an embodiment the hydrogel according to the invention is characterized in that the biological cells are pseudoislets.

The invention also concerns a therapeutic use of the hydrogel according to the invention for treating a disorder or disease in a mammal wherein the disorder or disease is due to lack or malfunction of endocrine function of pancreas organ.

The invention also concerns a hydrogel for use as a medicament.

The invention also concerns a hydrogel for use in the treatment of a disease such as diabetes.

The invention also concerns an implantable device comprising at least a hydrogel according to the invention and obtained according to the process of the invention.

The invention also concerns an implant consisting of the hydrogel according to the invention.

The invention also concerns an implant comprising the hydrogel according to the invention.

In an embodiment, at least 50% of the surface the hydrogel is directly in contact with the medium in which it is implanted.

In an embodiment, at least 75% of the surface the hydrogel is directly in contact with the medium in which it is implanted.

In an embodiment, at least 90% of the surface the hydrogel is directly in contact with the medium in which it is implanted.

In an embodiment, at least 95% of the surface the hydrogel is directly in contact with the medium in which it is implanted.

In an embodiment, 99% of the surface the hydrogel is directly in contact with the medium in which it is implanted.

In an embodiment, at least 50% of the surface the hydrogel is directly in contact with the exterior of the device or implant.

By «directly in contact with the exterior» means there is no separation between the hydrogel and the exterior, for example no wall made of a non-hydrogel material between the hydrogel and the exterior of the device or implant.

In an embodiment, at least 75% of the surface the hydrogel is directly in contact with the exterior of the device or implant.

In an embodiment, at least 90% of the surface the hydrogel is directly in contact with the exterior of the device or implant.

In an embodiment, at least 95% of the surface the hydrogel is directly in contact with the exterior of the device or implant.

In an embodiment, at least 99% of the surface the hydrogel is directly in contact with the exterior of the device or implant.

In an embodiment, 100% of the surface the hydrogel is directly in contact with the exterior of the device or implant.

The cells or the API are entrapped into the maze of cross-linked dextran hydrogel.

In this specification the word "entrapped" is equivalent to "encapsulated" or "encapsulation".

The hydrogel matrix allows passage of small molecules e.g. nutrients and API, API being entrapped into the hydrogel or secreted by the entrapped cells.

Typically, API are hormone and peptide drugs chosen amongst PTH protein, insulin and coagulation factors.

In an embodiment, the mesh size of the matrix is immunoisolant and stops the T lymphocytes in order to preserve the cells.

In an embodiment, this mesh size is less than 1 μm.

In another embodiment it is less that 100 nanometers, preferably less than 10 nanometers, and more preferably around 5 nanometers.

EXAMPLES

Part A—Chemistry

Example A1: Synthesis of substituted dextranmethylcarboxylate—maleimide (DMCMal) and dextranmethylcarboxylate—vinylsulfone (DMCVS)

TABLE 1

List of synthesized polysaccharides DMCMal and DMCVS

| Polysaccharides | Structure |
|---|---|
| Polysaccharide DMCMal-1 | 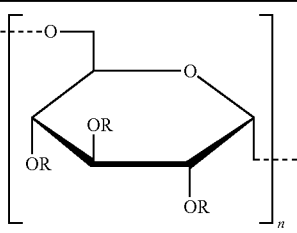<br>Mw (Dextran) = 40 kg/mol<br>n = 205<br>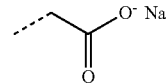<br>$DS_2 = 1.2$<br>$DS_1 = 0.24$ |
| Polysaccharide DMCMal-2 | 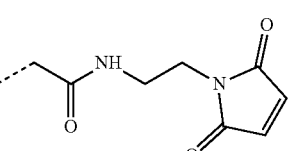<br>Mw (Dextran) = 40 kg/mol<br>n = 205<br>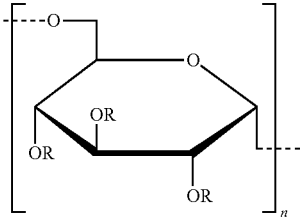<br>$DS_2 = 2.25$<br>$DS_1 = 0.24$ |
| Polysaccharide DMCMal-3 | 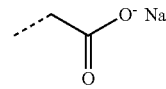<br>Mw (Dextran) = 500 kg/mol<br>n = 2200 |

TABLE 1-continued
List of synthesized polysaccharides DMCMal and DMCVS
| Polysaccharides | Structure |
|---|---|
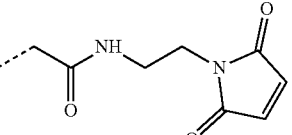
R = H or 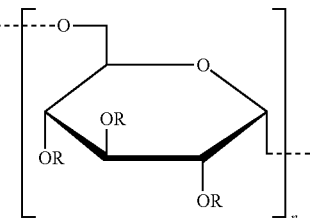 or 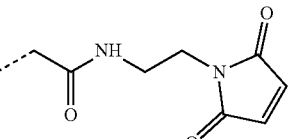
$DS_2 = 1.0$
$DS_1 = 0.25$
Polysaccharide DMCMal-4
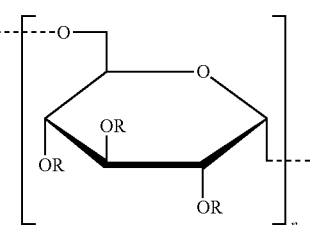
Mw (Dextran) = 500 kg/mol
n = 2200
R = H or 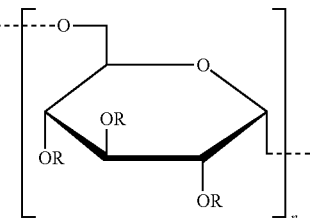 or 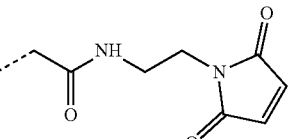
$DS_2 = 1.0$
$DS_1 = 0.09$
Polysaccharide DMCMal-5
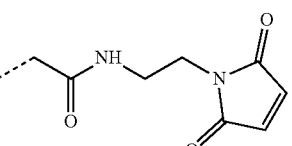
Mw (Dextran) = 250 kg/mol
n = 1100
R = H or 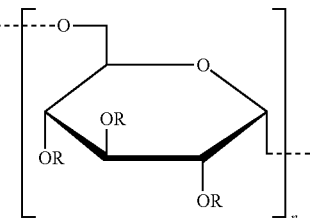 or 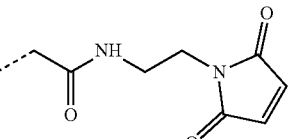
$DS_2 = 2.0$
$DS_1 = 0.25$
Polysaccharide DMCVS-1
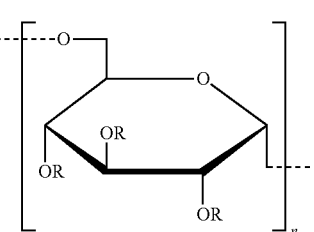
Mw (Dextran) = 40 kg/mol
n = 205

TABLE 1-continued

List of synthesized polysaccharides DMCMal and DMCVS

| Polysaccharides | Structure |
|---|---|

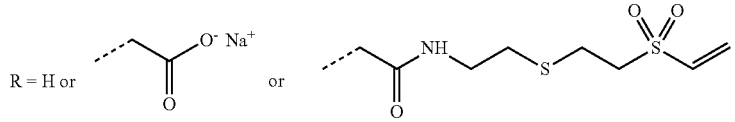

$DS_2 = 2.25$
$DS_1 = 0.25$

Polysaccharide DMCMal-1

Polysaccharide DMC-1

65 g (0.4 mol of glucoside units, 1.2 mol of hydroxyl functional groups) of dextran having a weight-average molar mass of 40 kg/mol (Pharmacosmos, degree of polymerization n=205), are dissolved in water (285 g/L) at 30° C., then $NaBH_4$ (74 mg, 1.95 mmol) is added and the mixture is stirred at 30° C. for 2 h. To this solution is added sodium chloroacetate (140 g, 1.2 mol) and the mixture is heated at 65° C. for 1 h. 10 N NaOH (200 mL, 2 mol) is then slowly added over 1.5 h and the mixture is stirred at 65° C. for 1 h. The mixture is diluted with water (120 mL), cooled to room temperature, neutralized with acetic acid and then purified by ultrafiltration on PES membrane (MWCO 5 kDa) against phosphate buffer pH 7, then water. The polysaccharide DMC-1 concentration of the final solution is determined by dry extract, and then an acid/base assay is carried out in order to determine the degree of substitution with methyl carboxylate.

According to the dry extract: [polysaccharide DMC-1]= 50.6 mg/g

According to the acid/base assay, degree of substitution with methylcarboxylate $(DS_2)$=1.2

Polysaccharide DMCMal-1

To 158 g of the solution of polysaccharide DMC-1 obtained above (50.6 mg/g, $DS_2$=1.2, 10.0 g of polysaccharide DMC-1, 38.73 mmol of glucoside units) 2-hydroxypyridine 1-oxide (HOPO) (4.30 g, 38.73 mmol) is added and the mixture is cooled to 4° C. To this solution are added N-(2-aminoethyl)maleimide hydrochloride (Mal) (2.05 g, 11.62 mmol), $Et_3N$ (1.62 mL, 11.62 mmol) and N-ethyl-N'-(3-dimethylaminopropyl)carbodiimide hydrochloride (EDC) (7.42 g, 38.73 mmol) and the reaction mixture is stirred at 4° C. for 4 h. Two additional additions of EDC (7.42 g, 38.73 mmol) are processed every 4 h. The mixture is diluted with phosphate buffer pH 7, then purified by ultrafiltration on PES membrane (MWCO 5 kDa) against phosphate buffer pH 7, NaCl (9 g/L) in water and then water. The polysaccharide DMCMal-1 concentration of the final solution is determined by dry extract, and the degree of substitution with maleimide is determined by $^1H$ NMR in $D_2O$. The final solution is stored at −20° C. or freezed-dried.

According to the dry extract: [polysaccharide DMCMal-1]=18.0 mg/g

According to $^1H$ NMR ($D_2O$), degree of substitution with maleimide $(DS_1)$=0.24

Polysaccharide DMCMal-2

Polysaccharide DMC-2

90 g (0.35 mol of glucoside units) of freeze-dried polysaccharide DMC-1 are dissolved in water (260 g/L) at 65° C., then sodium chloroacetate (204 g, 1.75 mol) is added and the mixture is maintained at 65° C. for 1 h. 10 N NaOH (175 mL, 1.75 mol) is then slowly added over 1 h and the mixture is stirred at 65° C. for a further 1 h. Another portion of sodium chloroacetate (122 g, 1.05 mol) is then added and the mixture is maintained at 65° C. for 0.5 h. 10 N NaOH (105 mL, 1.05 mol) is then slowly added over 1 h and the mixture is stirred at 65° C. for a further 1 h. The mixture is diluted with water, cooled to room temperature, neutralized with acetic acid and then purified by ultrafiltration on PES membrane (MWCO 5 kDa) against phosphate buffer pH 7, then water. The polysaccharide DMC-2 concentration of the final solution is determined by dry extract, and then an acid/base assay is carried out in order to determine the degree of substitution with methyl carboxylate.

According to the dry extract: [polysaccharide DMC-2]= 48.8 mg/g

According to the acid/base assay, degree of substitution with methylcarboxylate $(DS_2)$=2.25

Polysaccharide DMCMal-2

Using a process similar to the one used for the preparation of polysaccharide DMCMal-1, starting from polysaccharide DMC-2 (48.8 mg/g, $DS_2$=2.25, 10.0 g, 29.22 mmol of glucoside units) and with N-(2-aminoethyl) maleimide hydrochloride (1.55 g, 8.77 mmol), polysaccharide DMC-Mal-2 is obtained.

According to the dry extract: [polysaccharide DMCMal-2]=17.9 mg/g

According to $^1H$ NMR ($D_2O$), degree of substitution with maleimide $(DS_1)$=0.24.

Polysaccharide DMCMal-3

Polysaccharide DMC-3

Using a process similar to the one used for the preparation of polysaccharide DMC-1, starting from a dextran having a weight-average molar mass of 500 kg/mol, polysaccharide DMC-3 is obtained.

According to the dry extract: [polysaccharide DMC-3]= 34.3 mg/g

According to the acid/base assay, degree of substitution with methylcarboxylate $(DS_2)$=1.0

Polysaccharide DMCMal-3

Using a process similar to the one used for the preparation of polysaccharide DMCMal-1, starting from polysaccharide DMC-3 (34.3 mg/g, $DS_2$=1.0, 10.0 g, 41.29 mmol of glucoside units) and with N-(2-aminoethyl) maleimide hydrochloride (2.19 g, 12.39 mmol), polysaccharide DMCMal-3 is obtained.

According to the dry extract: [polysaccharide DMCMal-3]=12.0 mg/g

According to $^1$H NMR ($D_2O$), degree of substitution with maleimide ($DS_1$)=0.25

Polysaccharide DMCMal-4

Using a process similar to the one used for the preparation of polysaccharide DMCMal-1, starting from polysaccharide DMC-3 (34.3 mg/g, $DS_2$=1.0, 10.0 g, 41.29 mmol of glucoside units) and with N-(2-aminoethyl) maleimide hydrochloride (729 mg, 4.13 mmol), polysaccharide DMCMal-4 is obtained.

According to the dry extract: [polysaccharide DMCMal-4]=18.0 mg/g

According to $^1$H NMR ($D_2O$), degree of substitution with maleimide ($DS_1$)=0.09.

Polysaccharide DMCMal-5

Polysaccharide DMC-5

Using a process similar to the one used for the preparation of polysaccharide DMC-2, starting from a dextran having a weight-average molar mass of 250 kg/mol, polysaccharide DMC-5 is obtained.

According to the dry extract: [polysaccharide DMC-5]=47.6 mg/g

According to the acid/base assay, degree of substitution with methylcarboxylate ($DS_2$)=2.0

Polysaccharide DMCMal-5

Using a process similar to the one used for the preparation of polysaccharide DMCMal-1, starting from polysaccharide DMC-5 (47.6 mg/g, $DS_2$=2.0, 10.3 g, 31.98 mmol of glucoside units) and with N-(2-aminoethyl) maleimide hydrochloride (1.69 g, 9.59 mmol), polysaccharide DMCMal-5 is obtained.

According to the dry extract: [polysaccharide DMCMal-5]=18.3 mg/g

According to $^1$H NMR ($D_2O$), degree of substitution with maleimide ($DS_1$)=0.25

Polysaccharide DMCVS-1

To 205 g of the solution of polysaccharide DMC-2 (48.8 mg/g, $DS_2$=2.25, 10.0 g of polysaccharide DMC-2, 29.22 mmol of glucoside units), 2-hydroxypyridine 1-oxide (HOPO) (3.25 g, 29.22 mmol) is added and the mixture is cooled to 4° C. To this solution are added 2-[[2-(ethenylsulfonyl)ethyl]thio]ethanamine hydrochloride (VS) (2.03 g, 8.77 mmol), $Et_3N$ (1.83 mL, 13.15 mmol) and N-ethyl-N'-(3-dimethylaminopropyl)carbodiimide hydrochloride (EDC) (5.60 g, 29.22 mmol) and the reaction mixture is stirred at 4° C. for 4 h. Two additional additions of EDC (5.60 g, 29.22 mmol) are processed every 4 h. The mixture is diluted with carbonate buffer pH 9-10, stirred for 3 h, then purified by ultrafiltration on PES membrane (MWCO 5 kDa) against carbonate buffer pH 9-10, NaCl (9 g/L) in water, phosphate buffer pH 7, NaCl (9 g/L) in water, and then water. The polysaccharide DMCVS-1 concentration of the final solution is determined by dry extract, and the degree of substitution with vinyl sulfone is determined by $^1$H NMR in $D_2O$. The final solution is stored at −20° C. or freezed-dried.

According to the dry extract: [polysaccharide DMCVS-1]=20.7 mg/g

According to $^1$H NMR ($D_2O$), degree of substitution with vinyl sulfone ($DS_1$)=0.25

Example A2: Polyethylene Glycol Derivatives Comprising at Least Two Thiol Functions (Called in this Specification "PEG-SH")

Commercial Polyethylene glycol (PEG) derivatives functionalized with thiol (SH) groups were purchased. Linear homo bifunctional PEG-SH and multi-arm homofunctional PEG-SH having different molecular weights were used and are shown in the following Table 2.

TABLE 2

List of commercial PEG-SH used

| PEG-SH | Chemical Name | Thiol groups | Mn (kg/mol) |
|---|---|---|---|
| PEG-SH-1 | Poly (ethylene glycol) dithiol | 2 | 3.4 |
| PEG-SH-2 | Poly (ethylene glycol) dithiol | 2 | 1 |
| PEG-SH-3 | Pentaerythritol tetra(mercaptoethyl) polyoxyethylene | 4 | 5.2 |
| PEG-SH-4 | Pentaerythritol tetra(mercaptoethyl) polyoxyethylene | 4 | 20 |

Comparative Example A3 Polysaccharide Dextran Maleimide (DextranMal A3)

Commercial dextran derivative functionalized with maleimide (Mal) groups was purchased from Cellendes. The product is a kit containing 170 μL (volume after reconstitution) of Dextran-Mal with a concentration of maleimide functions of 30 mmol/L and 130 mg/mL polymer (concentrations after reconstitution). According to supplier the degree of substitution with maleimide was 0.046.

Part B—Biology

Example B1: Preparation of Pseudoislets

Beta-TC-tet cell line (ATCC) or Min-6 cell line (Caltag Medsystems) were cultivated in culture medium indicated in Table 3, in an incubator at 37° C. and 5% $CO_2$. Cells were subcultured 3 times a week using 0.05% trypsin/EDTA to detach the cells and diluted 5 times in culture medium.

TABLE 3

Culture media compositions
Culture media

| Beta-TC-tet | Min-6 |
|---|---|
| Dulbecco's Modified Eagle Medium (DMEM) | |
| 15% Horse Serum (HS) 2.5% Fœtal Bovine Serum (FBS) | 10% FBS |
| 1% penicillin/streptomycin | |
| 1 mM pyruvate | |
| — | 0.05 mM beta-mercaptoethanol |

Pseudoislets with a mean diameter of 150 μm were formed using Beta-TC-tet cell line using agarose 300 μm microwell moulds formed with Microtissue® templates (Sigma-Aldrich) by seeding 200 cells per microwell and incubating them at 37° C. and 5% $CO_2$ for 3 days. Pseudoislets were then collected, concentrated by centrifugation, and finally suspended in 0.9% NaCl.

Pseudoislets with a mean diameter of 150 μm were formed using Min-6 cell line using 400 μm microwell Eplasia plates (Corning) by seeding 500 cells per microwell and incubating them at 37° C. and 5% $CO_2$ for 3 days. Pseudoislets were then collected, concentrated by centrifugation, and finally suspended in 0.9% NaCl.

Example B2: Isolation of Primary Human Islets

Pancreata were obtained from human brain-dead donors. Pancreatic islets were produced following the method described in Technique of pancreatic procurement for pancreatic islet isolation, Pattou et al., Anchir 2005. Briefly, the pancreas was isolated from the tissue, and perfused in the Wirsung canal for digestion with a mix of collagenases I and II (Liberase®, Roche, France) in order to ensure the releasing of islets. Islets were then purified using a density grandient centrifugation (EuroFicoll, SigmaAldrich). Purified islets were finally cultured in culture flasks at 37° C. under 5% CO2 in either of the following medium:
Medium 1: CMRL medium (Gibco) supplemented with 0.1% BSA.
Medium 2: CMRL medium supplemented with 0.625% BSA and 1% penicillin/streptomycin Culture medium was replaced every 2-3 days.

Example B3: Primary Rat Islet Isolation

Pancreatic islets were isolated from male Wistar rats (approximative weight: 300 g) following a similar method as described in A Pratical Guide to Rodent Islet Isolation and Assessment, Carter et al. Biological Procedures Online 2009.

Briefly, pancreases were perfused with Collagenase injected via the common bile duct. After perfusion, pancreata were excised and the digestion was performed at 37° C. for 10 min. The islets were then purified through density gradient centrifugation. Purified islets were cultured in non adherent culture flasks, in RPMI medium (Gibco) supplemented with 10% Foetal Bovine Serum, 2 g/L glucose and 1% Penicillin/Streptomycin at 37° C. and 5% CO2. Culture medium was replaced every 2-3 days.

Example B4: Islet Equivalent Counting

To normalize the quantity of islets used in each experiment, islets or pseudoislets were counted to determine the islet equivalent count (IEQs). One IEQ corresponds to the volume of a perfectly spherical islet with a diameter of 150 μm. During counting, a multiplicative factor was applied to each islet depending on its size. This mathematical compensation for islet varying diameters allows for normalization between islet preparations (See NIH CIT Consortium Chemistry Manufacturing Controls Monitoring Committee; Purified Human Pancreatic Islet: Qualitative and Quantitative Assessment of Islets Using Dithizone (DTZ): Standard Operating Procedure of the NIH Clinical Islet Transplantation Consortium. CellR4 Repair Replace Regen Reprogram).

Two 50 μL samples from each islet or pseudoislet batch were counted on a glass slide with a 50 μm grid. Islets or pseudoislets were categorized by size according to Table 4.

TABLE 4

Multiplication factor of islet size for islet equivalent determination
The islet equivalent count was determined by averaging the count
results from two independent samples.

| Islet size | Multiplicative factor |
|---|---|
| 50-100 μm | 1/6 |
| 100-150 μm | 1/1.5 |
| 150-200 μm | 1.7 |
| 200-250 μm | 3.5 |
| 250-300 μm | 6.3 |

Part C—Physico-Chemistry

Example C1: Preparation of Solutions of Concentrated Polysaccharide DMCMal

A concentrated polysaccharide solution was prepared by weighing the appropriate weight of a sterile freeze-dried polysaccharide obtained according to part A1 and adding the appropriate weight of sterile deionised water. The solution was placed on an orbital shaker overnight at 70 rpm for complete solubilization. The pH of the solution was adjusted to pH 3, pH 4 or pH 5 by addition of concentrated HCl (4 mol/L). The mass concentration of the solution of polysaccharide DMCMal (mg/g) was determined by dry exact. The volume concentration of the solution of polysaccharide DMCMal (mg/mL) was determined by density measurements, weighing three times 100 μL of solution. The solution was frozen at −20° C. until being used.

Example C1A: Preparation of Solutions of Concentrated Polysaccharide DMCVS

A concentrated polysaccharide solution was prepared by weighing the appropriate weight of a sterile freeze-dried polysaccharide obtained according to part A1 and adding the appropriate weight of sterile deionised water. The solution was placed on an orbital shaker overnight at 70 rpm for complete solubilization. The pH of the solution was adjusted to pH 7.4 by addition of NaOH. The mass concentration of the solution of polysaccharide DMCVS (mg/g) was determined by dry extract. The volume concentration of the solution of polysaccharide DMCVS (mg/mL) was determined by density measurements, weighing three times 100 μL of solution. The solution was frozen at −20° C. until being used.

Example C2: Preparation of Solutions of Concentrated PEG-SH

A concentrated solution of PEG-SH (from the list according to table 2) was prepared by weighing the appropriate weight of a PEG-SH powder and adding the appropriate weight of sterile deionised water. The solution was placed on roller shaker at 15 rpm for 2 h for complete solubilization before sterile filtration (0.22 μm). The mass concentration of the PEG-SH solution (mg/g) was determined by dry extract. The volume concentration of the PEG-SH solution (mg/mL) was determined by density measurements, weighing three times 100 μL of solution. The solution was frozen at −20° C. until being used.

Example C3: Hydrogel Preparation—1

The preparation of the hydrogel was made in an aseptic environment.

Polysaccharide DMCMal and PEG-SH concentrated sterile solutions prepared according to example C1 and C2 respectively were equilibrated either at room temperature (20-25° C.) or at 4° C.

225 µL of a concentrated solution of PEG-SH was added to 225 µL of a concentrated solution of polysaccharide DMCMal in a 2 mL Eppendorf. The solutions were mixed with a pipette and 200 µL of mixture were introduced in a rectangular silicone mould (IBIDI 12×7.75 mm). Gelation was carried out for 1 h at room temperature (20-25° C.). The hydrogel was unmoulded and introduced in a 10 mL PBS (phosphate buffer saline) solution at pH 7.4 for 2 h at 37° C. Optionally the PBS solution contains 10 mM of cysteine. The hydrogel was rinsed with a 10 mL of PBS solution without cysteine and further immersed in 20 mL of the PBS solution overnight at 37° C. The hydrogel piece was then stored in 10 mL of PBS solution at 4° C. until being used.

20 µL of a concentrated solution of PEG-SH was added to 20 µL of a concentrated solution of polysaccharide DMCMal or DMCVS in a 2 mL Eppendorf. The solutions were mixed with a pipette and a controlled volume of the mixture (32 µL) was introduced in a circular silicone isolator (9 mm diameter/0.5 mm thick, from Grace Biolab) adhering to a glass slide.

Gelation was carried out for 1 h at room temperature (20-25° C.) or at 37° C. The hydrogel was unmoulded and introduced in a Tris 150 mM/NaCl 30 mM/Cystein 10 mM solution (2 mL) at pH 8 for 1 h15 at 37° C. The hydrogel was rinsed with 20 mL of PBS solution without cysteine and further immersed in 10 mL of the PBS solution overnight at 37° C. The hydrogel piece was then stored in 10 mL of PBS solution at 4° C. until being used.

Example C4: Hydrogel Compositions—1

Different hydrogel compositions were prepared according to the protocol described in Example C3 (Table 3). Concentrations of reactive groups (maleimide (Mal) and thiol (SH)) and polymers (polysaccharide DMCMal and PEG-SH) correspond to the final concentration upon mixing of the polymer solutions.

TABLE 5

Compositions of various hydrogels made of a DMCMal polysaccharide and a PEG-SH

| Example | Polysaccharide DMCMal | PEG-SH | Mal: SH (mM:mM) | [DMCMal] (mg/mL) | pH | [PEG-SH] (mg/mL) | Mixing Temperature (° C.) |
|---|---|---|---|---|---|---|---|
| C4-1* | DMCMal-1 | PEG-SH-1 | 18:18 | 22.8 | 4 | 35.1 | 20-25 |
| C4-2* | DMCMal-1 | PEG-SH-1 | 40:40 | 50.7 | 4 | 78.1 | 20-25 |
| C4-3* | DMCMal-2 | PEG-SH-1 | 36:36 | 54.9 | 4 | 70.3 | 20-25 |
| C4-4 | DMCMal-2 | PEG-SH-1 | 36:36 | 54.9 | 4 | 70.3 | 20-25 |
| C4-5 | DMCMal-2 | PEG-SH-2 | 72:72 | 109.9 | 4 | 42.7 | 4 |
| C4-6 | DMCMal-2 | PEG-SH-3 | 36:36 | 54.9 | 4 | 49.2 | 4 |
| C4-7 | DMCMal-2 | PEG-SH-4 | 10:10 | 13.1 | 4 | 54 | 4 |
| C4-8 | DMCMal-2 | PEG-SH-4 | 10:10 | 13.1 | 5 | 54 | 4 |
| C4-9 | DMCMal-2 | PEG-SH-4 | 18:18 | 23.5 | 4 | 97.2 | 4 |
| C4-10* | DMCMal-4 | PEG-SH-1 | 19:19 | 53 | 4 | 37.1 | 20-25 |
| C4-11 | DMCMal-3 | PEG-SH-1 | 40:40 | 42.4 | 4 | 78.1 | 4 |

*Compositions not having been washed with PBS solution comprising cysteine.

Example C3A: Hydrogels Preparation—2

The preparation of the hydrogels was made in an aseptic environment.

Polysaccharide DMCMal or DMCVS and PEG-SH concentrated sterile solutions prepared according to example C1 or C1A and example C2, respectively, were adjusted with a concentrated NaCl solution in order to obtain isotonic stock solutions (300 mOsm/kg) and equilibrated either at room temperature (20-25° C.) or at 4° C. Optionally DMCVS concentrated solutions was supplemented by a tris buffer at pH 7.4 or pH 8.

Solid rectangular hydrogel pieces were obtained. The 12×7.75×2.1 mm hydrogels pieces were easily unmoulded and handled with tweezers for characterization.

Example C4A: Hydrogel Compositions—2

Different hydrogel compositions were prepared according to the protocol described in Example C3A (Table 3). Concentrations of reactive groups (maleimide (Mal) or Vinylsulfone (VS) and thiol (SH)) and polymers (polysaccharide DMCMal or DMCVS and PEG-SH) correspond to the final concentration upon mixing of the polymer solutions.

TABLE 6

Compositions of hydrogels made of a DMCMal or DMCVS polysaccharide and a PEG-SH polymer

| Example | Polysaccharide | PEG-SH | Mal or VS: SH (mM:mM) | [Polysaccharide] (mg/mL) | pH | Tris buffer (mM) | [PEG-SH] (mg/mL) | Mixing Temperature (° C.) | Gelling temperature (° C.) |
|---|---|---|---|---|---|---|---|---|---|
| C4A-1 | DMCMal-5 | PEG-SH-4 | 10:10 | 13.4 | 4 | — | 56.4 | 4 | 20-25 |
| C4A-2 | DMCVS-1 | PEG-SH-4 | 18:18 | 24.1 | 7,4 | — | 101.5 | 20-25 | 37 |

TABLE 6-continued

Compositions of hydrogels made of a DMCMal or DMCVS polysaccharide and a PEG-SH polymer

| Example | Polysaccharide | PEG-SH | Mal or VS: SH (mM:mM) | [Polysaccharide] (mg/mL) | pH | Tris buffer (mM) | [PEG-SH] (mg/mL) | Mixing Temperature (° C.) | Gelling temperature (° C.) |
|---|---|---|---|---|---|---|---|---|---|
| C4A-3 | DMCVS-1 | PEG-SH-4 | 18:18 | 24.1 | 7,4 | 6 | 101.5 | 20-25 | 37 |
| C4A-4 | DMCVS-1 | PEG-SH-4 | 18:18 | 24.1 | 7,4 | 6 | 101.5 | 20-25 | 20-25 |
| C4A-5 | DMCVS-1 | PEG-SH-4 | 18:18 | 24.1 | 8 | 6 | 101.5 | 20-25 | 37 |
| C4A-6 | DMCVS-1 | PEG-SH-4 | 14:14 | 18.7 | 8 | 6 | 78.9 | 20-25 | 20-25 |

Solid disc-shaped hydrogel pieces were obtained. The hydrogels pieces (9 mm diameter/0.5 mm thick) were easily unmoulded and handled with tweezers for characterization.

Example C4': Hydrogel Rheological Characterization

Oscillatory shear test was carried out with a rotational rheometer (AR2000, TA instrument) equipped with a cone plate geometry. The gelation was done "in situ", meaning that drops of polysaccharide and PEG concentrated solutions were introduced between cone one and plate and mixed by rotation of the geometry before starting oscillations measurements. Oscillation time sweep tests were carried out at 25° C. or 37° C., with a constant strain of 0.1% and constant oscillation frequency of 1 Hz. The storage modulus G' (i.e. elastic modulus) and Tan δ (ratio G'/G") values were reported at 1600 s in the plateau region of the measure of (G',G") as a function of time.

This can allow a fine tuning of the gelation speed which could be convenient as fast gelation could be beneficial to avoid cells sedimentation whereas slow gelation could be beneficial for polymer mix casting before gelation.

Example C5: Hydrogel Swelling and Water Content

The hydrogel piece was weighed right after unmoulding ($w_0$) and after overnight swelling ($w_{overnight}$) in the PBS solution. The swelling ratio was defined as the mass ratio $w_{overnight}/w_0$. The water content of the hydrogel was deducted from the measurement of hydrogel mass in the swollen state and the control of polymer precursors concentrations implemented to synthetize the hydrogel.

TABLE 4

Results of hydrogel rheological characterization.

| Example | Mal: SH or Mal:VS (mM:mM) | [DMCMal] or [DMCVS] (mg/mL) | pH | Tris buffer (mM) | [PEG-SH] (mg/mL) | Temperature (° C.) | Gelation onset (min) (time G' > 1 Pa) | G' (kPa) 1600s | G' (kPa) 3600s | Tan δ (G'/G") |
|---|---|---|---|---|---|---|---|---|---|---|
| C4-1 | 18:18 | 22.8 | 4 | — | 35.1 | 25 | <2 | 8.4 | NA | <0.01 |
| C4-2 | 40:40 | 50.7 | 4 | — | 78.1 | 25 | <1 | 17.6 | NA | <0.01 |
| C4-4 | 36:36 | 54.9 | 4 | — | 70.3 | 25 | <1 | 23.8 | NA | <0.01 |
| C4-5 | 72:72 | 109.9 | 4 | — | 42.7 | 25 | <0.5 | 54 | NA | <0.01 |
| C4-6 | 36:36 | 54.9 | 4 | — | 49.2 | 25 | <0.5 | 59.7 | NA | <0.01 |
| C4-7 | 10:10 | 13.1 | 4 | — | 54 | 25 | <2 | 12.7 | NA | <0.01 |
| C4-8 | 10:10 | 13.1 | 5 | — | 54 | 25 | <0.5 | 18 | NA | <0.01 |
| C4-9 | 18:18 | 23.5 | 4 | — | 97.2 | 25 | <1 | 38 | NA | <0.01 |
| C4-10 | 19:19 | 53 | 4 | — | 37.1 | 25 | <2 | 4.9 | NA | <0.01 |
| C4-11 | 40:40 | 42.4 | 4 | — | 78.1 | 25 | <0.5 | 17.5 | NA | <0.01 |
| C4A-1 | 10:10 | 13.4 | 4 | — | 56.4 | 25 | <1.5 | 7.9 | 10 | <0.01 |
| C4A-2 | 18:18 | 24.1 | 7,4 | — | 101.5 | 37 | >4 | 5.4 | 15 | <0.01 |
| C4A-3 | 18:18 | 24.1 | 7,4 | 6 | 101.5 | 37 | >3 | 7.2 | 17 | <0.01 |
| C4A-4 | 18:18 | 24.1 | 7,4 | 6 | 101.5 | 25 | >8 | 1 | 4.3 | <0.01 |
| C4A-5 | 18:18 | 24.1 | 8 | 6 | 101.5 | 37 | <1 | 9.6 | 23.8 | <0.01 |
| C4A-6 | 14:14 | 18.7 | 8 | 6 | 78.9 | 25 | <2 | 9.5 | 15.8 | <0.01 |

Hydrogels present low values of Tan δ, meaning that G' was much higher than G" which is a typical property of chemically cross-linked hydrogels behaving as solid elastic materials (see Polysaccharide Hydrogels: Characterization and Biomedical Applications, 2016 Pan Stanford Publishing Pte. Ltd.; Chapter 3, page 97). The increase of the concentration in Mal:SH leads to an increase of the value of elastic modulus G'.

Increasing the temperature and the pH were two ways to accelerate the gelation of hydrogels prepared from DMCVS and PEG-SH. For example, going from neutral pH to pH 8 and/or increasing the temperature from 25° C. to 37° C. leads to a faster gelation.

TABLE 7

Hydrogel swelling and water content.

| Example | Hydrogel Composition | swelling ratio | Water content (weight %) |
|---|---|---|---|
| C5-1 | C4-1 | 1.2 | 95.2 |
| C5-2 | C4-2 | 1.7 | 92.4 |
| C5-3 | C4-3 | 1.7 | 92.8 |
| C5-4 | C4-4 | 1.8 | 93.2 |

TABLE 7-continued

Hydrogel swelling and water content.

| Example | Hydrogel Composition | swelling ratio | Water content (weight %) |
|---|---|---|---|
| C5-5 | C4-5 | 1.8 | 91.5 |
| C5-6 | C4-6 | 1.3 | 91.9 |
| C5-7 | C4-7 | 1.2 | 94.2 |
| C5-8 | C4-8 | 1.2 | 94.2 |
| C5-9 | C4-9 | 1.7 | 92.8 |
| C5-10 | C4-10 | 2.6 | 96.6 |
| C5-11 | C4-11 | 1.4 | 93.5 |
| C5-12 | C4A-1 | 1.3 | 94.6 |
| C5-13 | C4A-2 | 1.3 | 90.3 |

Hydrogels contain high water content. Water content varies depending on polymer precursors structures and concentrations.

Example C6: Hydrogel Stability at 37° C. in Physiological Medium

Hydrogel pieces were stored in PBS at pH 7.4 or in Serum (FBS Foetal Bovine Serum) at 37° C. and weighed at different periods of time.

In example C6-1 and C6-2, rectangular hydrogel pieces of 12×8×2.1 mm were used. In example C6-3 disc-shaped hydrogels with a diameter of 9 mm and a thickness of 1.6 mm were tested.

TABLE 8

Hydrogel stability in physiological medium

| Example | Hydrogel composition | medium | number of hydrogels weighed | Time at 37° C. (days) | Gel Mass (mg) |
|---|---|---|---|---|---|
| C6-1 | C4-2 | PBS | 3 | 0 | 312 ± 4 |
|  |  |  |  | 22 | 316 ± 7 |
|  |  |  |  | 77 | 310 ± 6 |
| C6-2 | C4-5 | PBS | 1 | 0 | 324 |
|  |  |  |  | 120 | 326 |
|  |  | Serum | 1 | 0 | 329 |
|  |  |  |  | 120 | 332 |
| C6-3 | C4A-1 | PBS | 3 | 0 | 132 ± 4 |
|  |  |  |  | 30 | 134 ± 1 |
|  |  |  |  | 60 | 139 ± 2 |
| C6-4 | C4A-2 | PBS | 3 | 0 | 179 ± 9 |
|  |  |  |  | 30 | 183 ± 13 |
|  |  |  |  | 60 | 189 ± 10 |

Hydrogels were retrieved intact and their mass does not evolve significantly upon storage at 37° C. in physiological medium. Hydrogel swelling (mass increase) or dissolution (mass decrease) would be expected in case of network structure modification in case of hydrolysis side reaction for example. This shows that the hydrogel was stable under physiological conditions.

Example C7: Encapsulation of Macromolecular Probes within Hydrogel

Commercial Fluorescent Dextran-FITC 3 kDa and Dextran-FITC 70 kDa were each solubilised in water to obtain concentrated stock solutions.

Polysaccharide DMCMal and PEG-SH concentrated sterile solutions prepared according to example C1 and C2, respectively, were equilibrated at 4° C. For DMCVS based hydrogel, polysaccharide DMCMal and PEG-SH concentrated solutions prepared according to example C1A and C2, respectively, were equilibrated at 20-25° C.

The solution of polysaccharide DMCMal or DMCVS was mixed with a fluorescent dextran. 100 µL of a concentrated solution of PEG-SH was added to 100 µL of a concentrated solution of polysaccharide DMCMal or DMCVS and fluorescent dextran. The solutions were mixed with a pipette and 200 µL of the latter mixture was introduced in a rectangular silicone mould (IBIDI 12×7.75 mm). Gelation was carried out for 1 h at room temperature (20-25° C.) for DMCMal based hydrogel or 1 h at 37° C. for DMCVS based hydrogel.

The hydrogel piece was unmoulded, introduced in a well (12 wells multi-plate) and immersed with 1.3 mL of a buffer solution of Tris (200 mM)/NaCl (50 mM) at pH 8 containing the same concentration of encapsulated fluorescent dextran. Hydrogel swelling was performed overnight at 37° C. and the supernatant was weighed to estimate the degree of swelling and the quantity (mg) in the hydrogel volume.

Hydrogels were quickly rinsed twice with 1 mL of a buffer solution of Tris (200 mM)/NaCl (50 mM) at pH 8 before release experiment (shown in example C8).

TABLE 9

Compositions of hydrogel with encapsulated fluorescent macromolecular probe

| Example | Polysaccharide DMCMal or DMCVS | PEG-SH | Mal or VS: SH (mM:mM) | [Polysaccharide DMCMal or DMCVS] (mg/mL) | pH | [PEG-SH] (mg/mL) | Dextran (kda) | [Dextran] (mg/mL) |
|---|---|---|---|---|---|---|---|---|
| C7-1 | DMCMal-2 | PEG-SH-1 | 36:36 | 54.9 | 4 | 70.3 | 3 | 1.5 |
| C7-2 | DMCMal-2 | PEG-SH-1 | 36:36 | 54.9 | 4 | 70.3 | 70 | 1.5 |
| C7-3 | DMCMal-5 | PEG-SH-4 | 10:10 | 13.4 | 4 | 56.4 | 3 | 1.5 |
| C7-4 | DMCMal-5 | PEG-SH-4 | 10:10 | 13.4 | 4 | 56.4 | 70 | 1.5 |
| C7-5 | DMCVS-1 | PEG-SH-4 | 18:18 | 24.1 | 7.4 | 101.5 | 3 | 1.5 |
| C7-6 | DMCVS-1 | PEG-SH-4 | 18:18 | 24.1 | 7.4 | 101.5 | 70 | 1.5 |

Example C8: Release of Macromolecular Probes within Hydrogel

Hydrogels with encapsulated fluorescent probe as produced in Example C7 were each introduced in a well (12 wells multi-plate) and immersed with 2 mL of a buffer solution of Tris (200 mM)/NaCl (50 mM) at pH 8. The plate was covered with a film and introduced in an oven at 37° C. 200 µL of buffer were sampled at different time point and replaced by fresh buffer. Fluorescent probe concentration in the samples was determined by fluorescence (fluorescent plate reader SAFAS) using a calibration curve. The cumulative fraction of fluorescent probe released at each time point corresponds to the ratio of the cumulative quantity of fluorescent probe released to the initial quantity of fluorescent probe in the swollen hydrogel.

TABLE 10

Cumulative fraction of macromolecular probes released from the hydrogel at different time points.

| Composition | Time (h) | 0.25 | 0.5 | 1 | 2 | 6 | 72 |
|---|---|---|---|---|---|---|---|
| C7-1 | % Dextran 3 kDa released | 8.8 | 12 | 17.5 | 24 | 30.3 | 32 |
| C7-2 | % Dextran 70 kDa released | 0.3 | 0.7 | 1.2 | 1.8 | 3.8 | 4.8 |
| C7-3 | % Dextran 3 kDa released | 7.6 | 10.7 | 17.1 | 24.1 | 34.5 | 39.1 |
| C7-4 | % Dextran 70 kDa released | nm* | nm* | nm* | nm* | nm* | 12.5 |
| C7-5 | % Dextran 3 kDa released | 5.2 | 9.5 | 13.7 | 19.2 | 30.9 | 35.1 |
| C7-6 | % Dextran 70 kDa released | nm* | nm* | nm* | nm* | 1.5 | 10.1 | nm*: not measured

Increasing the size of the macromolecular probe leads to a slower kinetic of release. This shows the permselective property of the hydrogel's network structure.

Example C9: Encapsulation of Beta-TC-Tet Pseudo Islets in Hydrogels

Pseudo islets encapsulation was made in an aseptic environment.

Polysaccharide DMCMal and PEG-SH concentrated sterile solutions prepared according to examples C1 and C2, respectively, were adjusted with a concentrated NaCl solution in order to obtain isotonic stock solutions (300 mOsm/kg). Solutions were equilibrated either at room temperature (20-25° C.) or at 4° C.

A concentrated mixture of PEG-SH and pseudo islets was prepared by mixing equal volumes of isotonic PEG-SH solution and pseudo islets suspension (prepared according to example B1). Then the mixture containing PEG-SH and pseudo islets was gently mixed with an equivalent volume of isotonic concentrated solution of polysaccharide DMCMal using a pipette.

The mixture containing the polysaccharide DMCMal, PEG-SH and pseudo islets was introduced in a mould, such as a rectangular silicone mould (IBIDI 12×7.75 mm) or in multiwell plate.

Gelation was carried out for 30 min at room temperature (20-25° C.). Rectangular hydrogel piece was unmoulded and introduced in a multiwell plate. Gel formed in the multiwell plate was kept at room temperature.

For neutralization, 2 mL of a buffer solution of Tris (200 mM)/NaCl (50 mM) at pH 8 was added to the wells containing the gels for 15 min at room temperature (20-25° C.).

The Tris buffer solution was replaced with 2 mL of culture medium containing 1 µg/mL of tetracycline to stop the cell proliferation. The hydrogel was incubated at 37° C. and 5% $CO_2$ before further use.

Different hydrogel compositions were prepared according to this process. Concentrations of reactive groups (Maleimide and Thiol) and polymers (polysaccharide DMCMal and PEG-SH) correspond to the final concentration upon mixing of the polymer solutions in presence of pseudo islets.

TABLE 11

Compositions of hydrogels containing encapsulated pseudo islets

| Example | Polysaccharide DMCMal | PEG-SH | Mal:SH (mM:mM) | [polysaccharide DMCMal] (mg/mL) | pH | [PEG-SH] (mg/mL) | Mixing Temperature (° C.) | Pseudo islets density (islets/mL) | Mould used |
|---|---|---|---|---|---|---|---|---|---|
| C9-1 | DMCMal-1 | PEG-SH-1 | 30:30 | 35.5 | 4 | 58.4 | 20-25 | 575 | 24-Well plate |
| C9-2 | DMCMal-1 | PEG-SH-2 | 40:40 | 47.3 | 4 | 23.8 | 4 | 470 | 12 × 7.75 mm |
| C9-3 | DMCMal-1 | PEG-SH-2 | 55:55 | 65 | 4 | 32.8 | 4 | 470 | 12 × 7.75 mm |
| C9-4 | DMCMal-1 | PEG-SH-2 | 72:72 | 85.1 | 4 | 42.9 | 4 | 470 | 12 × 7.75 mm |

Example C10: Moulding of Thin Hydrogel Discs

According to the protocol described for example C3, concentrated polymer solutions were equilibrated at 4° C. The solutions were mixed with a pipette and a controlled volume of the mixture was introduced in a circular silicone isolator (9 mm diameter/0.5 mm thick, from Grace Biolab) adhering to a glass slide.

Upon 15 min gelation at 20-25° C. hydrogel discs were unmoulded and weighed right after unmoulding ($w_0$) and after overnight swelling ($w_{overnight}$) in PBS at 37° C. The swelling ratio is defined as the mass ratio $w_{overnight}/w_0$. The diameter of the swollen hydrogel was measured with a caliper. The thickness was deduced from the measured diameter and weight of the disc.

TABLE 12

Thickness of compositions of hydrogels containing encapsulated pseudo islets

| Example | Polysaccharide DMCMal | PEG-SH | Mal:SH (mM:mM) | pH | Mixing Temperature (° C.) | Initial Volume (μL) | Swelling ratio | Diameter (mm) | Thickness (mm) |
|---|---|---|---|---|---|---|---|---|---|
| C10-1 | DMCMal-2 | PEG-SH-4 | 18:18 | 4 | 4 | 40 | 1.7 | 10.9 | 0.83 |
| C10-2 | DMCMal-2 | PEG-SH-4 | 18:18 | 4 | 4 | 32.5 | 1.9 | 11.2 | 0.66 |
| C10-3 | DMCMal-2 | PEG-SH-4 | 18:18 | 4 | 4 | 25 | 1.8 | 10.7 | 0.52 |

The method allows to obtain hydrogels discs of controlled diameters and thicknesses by adjusting the diameter of the mould and the volume of hydrogel.

Example C11: Determination of Mechanical Resistance of the Hydrogels

For compression, a swollen rectangular hydrogel piece as described in example C3 was introduced in a flat glass crystallizer and immersed in PBS. The uniaxial compression was done in PBS a 20-25° C. by using axial force sensor of an AR2000 rheometer equipped with a flat compression plate, at a speed of 0.6 mm/min. Initial thickness of the sample was determined from the contact of the plate with the hydrogel, when the force starts to increase. The deformation is defined by the ratio of the compression displacement (mm) and the initial thickness (mm). The deformation at break was determined from the force/displacement curve. The break is defined when a decrease of the force versus displacement was observed.

For traction, dog bone shaped hydrogel pieces were prepared by moulding hydrogel in a dog bone shaped silicone mould. The uniaxial traction was done in air at 20-25° C. a with a universal mechanical tester apparatus (Instron or Zwickroell) equipped with screw grips, at a speed of 3 mm/min. Initial length of the sample was measured between the grips with a ruler. The deformation is defined by the ratio of the traction displacement (mm) and the initial length (mm). The deformation at break was determined from the force/displacement curve. The break is defined when a decrease of the force versus displacement was observed. The Young modulus was determined from the slope of the true strain/deformation curve. The true strain (kPa) corresponds to the ratio of the force (N) to the instantaneous surface area ($mm^2$) of the sample under compression.

The hydrogels according to the invention exhibit very good mechanical resistances features combining deformability and stiffness suitable for surgical implantation.

Example C15: Encapsulation of Insulin Producing Cell Islets in Hydrogels

Cell islets encapsulation was made in an aseptic environment.

Polysaccharide DMCMal or DMCVS and PEG-SH concentrated sterile solutions prepared according to examples C1 or C1A and C2, respectively, were adjusted with a concentrated NaCl solution in order to obtain isotonic stock solutions (300 mOsm/kg). Solutions were equilibrated either at room temperature (20-25° C.) for DMCVS based hydrogels or at 4° C. for DMCMal hydrogels.

A concentrated mixture of PEG-SH and islets was prepared by mixing equal volumes of isotonic PEG-SH solution islets suspension (prepared according to example B1, B2, B3, and/or B4). Then the mixture containing PEG-SH and islets was gently mixed with an isotonic concentrated solution of polysaccharide DMCMal or DMCVS by a 70:30 Volume:Volume proportion of islets suspension/PEG-SH: polysaccharide.

The solutions were gently mixed with a pipette and a controlled volume of the mixture was introduced in a circular silicone isolator from Grace Biolab) adhering to a glass slide. Different hydrogel sizes were made depending on the volume and silicone mould diameter.

TABLE 14

Moulded hydrogels volume and size

| Volume (μL) | Mould Diameter (mm) |
|---|---|
| 10 | 4.5 |
| 32 | 9 |
| 66 or 70 | 13 |
| 160 | 20 |

Gelation was carried out for 1 h at room temperature (20-25° C.) or at 37° C. The hydrogel incorporating islets

TABLE 13

Mechanical resistance of hydrogels

| Example | Composition | Polysaccharide DMCMal or DMCVS | PEG-SH | Mal or VS:SH (mM:mM) | pH | Mixing Temperature (° C.) | Compression Deformation at break (%) | Compression Young Modulus (kPa) | Traction Deformation at break (%) | Traction Young Modulus (kPa) |
|---|---|---|---|---|---|---|---|---|---|---|
| C11-1 | C4-9 | DMCMal-2 | PEG-SH-4 | 18:18 | 4 | 4 | >60 | >50 | >40 | >50 |
| C11-2 | C4A-1 | DMCMal-5 | PEG-SH-4 | 10:10 | 4 | 4 | >60 | >30 | >40 | >30 |
| C11-3 | C4A-2 | DMCVS-1 | PEG-SH-4 | 18:18 | 7.4 | 20-25 | >60 | >50 | >40 | >50 | was unmoulded and introduced in a Tris 150 mM/NaCl 30 mM/Cystein 10 mM solution at pH 8 for 15 min at room temperature. Hydrogels were then immersed in culture medium containing 10 mM cysteine for 1 h at 37° C. After 1 h the culture medium containing cysteine was removed and replaced by culture medium. Sterile hydrogels containing cells were stored at 37° C. and 5% $CO_2$ before further in vitro testing or in vivo implantation.

Different hydrogel compositions were prepared according to this process, either with pseudo islets or primary islets. Concentrations of reactive groups (Maleimide or Vinylsulfone and Thiol) and polymers (polysaccharide DMCMal and PEG-SH) correspond to the final concentration upon mixing of the polymer solutions in presence of islets.

TABLE 15

Moulded hydrogels volume and size

| Example | Polysaccharide | PEG-SH | Mal:SH (mM:mM) | pH | Gelation Temperature (° C.) | Islets or pseudo islets type | islets density (islets equivalent/mL) | Hydrogel Volume (μL) |
|---|---|---|---|---|---|---|---|---|
| C15-1 | DMCMal-5 | PEG-SH-4 | 10:10 | 4 | 20-25 | MIN-6 | 20,000 | 10 |
| C15-2 | DMCMal-5 | PEG-SH-4 | 10:10 | 4 | 20-25 | MIN-6 | 40,000 | 10 |
| C15-3 | DMCMal-5 | PEG-SH-4 | 10:10 | 4 | 20-25 | Rat | 20,000 | 10 |
| C15-4 | DMCMal-1 | PEG-SH-2 | 72:72 | 4 | 20-25 | Human | 20,000 | 10 |
| C15-5 | DMCMal-2 | PEG-SH-4 | 18:18 | 4 | 20-25 | Human | 20,000 | 10 |
| C15-6 | DMCMal-5 | PEG-SH-4 | 10:10 | 4 | 20-25 | Human | 5,000 | 66 |
| C15-7 | DMCMal-5 | PEG-SH-4 | 10:10 | 4 | 20-25 | Human | 20,000 | 10 |
| C15-8 | DMCMal-5 | PEG-SH-4 | 10:10 | 4 | 20-25 | Human | 40,000 | 10 |
| C15-9 | DMCVS-1 | PEG-SH-4 | 18:18 | 7,4 | 37 | Human | 20,000 | 10 |
| C15-10 | DMCMal-5 | PEG-SH-4 | 10:10 | 4 | 20-25 | Human | 33,000 | 32 |
| C15-11 | DMCMal-5 | PEG-SH-4 | 10:10 | 4 | 20-25 | Mouse | 33,000 | 32 |
| C15-12 | DMCMal-5 | PEG-SH-4 | 10:10 | 4 | 20-25 | Human | 38,000 | 66 |
| C15-13 | DMCMal-5 | PEG-SH-4 | 10:10 | 4 | 20-25 | Rat | 33,000 | 70 |

Comparative Example CE16: Preparation of Carboxymethyl Dextran-Based Hydrogel Cross-Linked with EDC A concentrated polysaccharide solution was prepared by weighing the appropriate weight of a sterile freeze-dried polysaccharide DMC-3 obtained according to part A1 and adding the appropriate weight of deionised water.

A concentrated solution of EDC/NHS coupling agents was prepared by dissolving EDC and NHS powders in deionised water.

The EDC/NHS concentrated solution was added to the concentrated solution of polysaccharide in a 3 mL glass vial to obtain the desired composition (Table 15). A clear and non-viscous solution was obtained. The vial was placed on a roller shaker for 30 min at room temperature (20-25° C.). A viscous solution was obtained. A controlled volume of the mixture (100 μL) was introduced in a circular silicone isolator (9 mm diameter/2 mm thick, from Grace Biolab) adhering to a glass slide. Gelation was pursued for 45 min at 37° C.

The hydrogel was unmoulded and introduced in a Tris 150 mM/NaCl 30 mM (2 mL) at pH 8 for 1 h at 37° C. Tris/NaCl was replaced by PBS and the hydrogel was stored overnight at 37° C. before mechanical testing.

TABLE 16

Carboxymethyl dextran-based hydrogel cross-linked with EDC/NHS

| Example | Polysaccharide type | Polysaccharide (mg/mL) | Cross-linker | EDC (mg/g) | NHS (mg/g) |
|---|---|---|---|---|---|
| CE16-1 | DMC-3 | 120 | EDC/NHS | 35.5 | 5.5 |

Example C17: Preparation of DMC-Mal Based Hydrogel Cross-Linked with DTT (Dithiothreitol), Comparative Example, or PEG-SH Polysaccharide DMCMal and PEG-SH concentrated solutions prepared according to example C1 and example C2, respectively, were adjusted with a concentrated NaCl solution in order to obtain isotonic stock solutions (300 mOsm/kg) and equilibrated at 4° C.

Concentrated DTT solution was prepared by dissolution of DTT powder in water and a concentrated NaCl solution in order to obtain isotonic stock solutions (300 mOsm/kg) and equilibrated at 4° C.

112 μL of a concentrated solution of DTT or PEG-SH was added to 112 μL of a concentrated solution of polysaccharide DMCMal in a 2 mL Eppendorf. The solutions were mixed with a pipette and a controlled volume of the mixture (100 μL) were introduced in a circular silicone isolator (9 mm diameter/2 mm thick, from Grace Biolab) adhering to a glass slide. Gelation was carried out for 1 h at room temperature (20-25° C.). The hydrogel was unmoulded and introduced in a Tris 150 mM/NaCl 30 mM (2 mL) at pH 8 for 1 h at 37° C. Tris/NaCl was replaced by PBS and the hydrogel was stored overnight at 37° C. before mechanical testing.

TABLE 17

DMC-Mal based hydrogel cross-linked with DTT or PEG-SH

| Example | Polysaccharide type | Cross-linker | Mal: SH (mM:mM) | Polysaccharide (mg/mL) | pH | Cross-linker mg/mL |
|---|---|---|---|---|---|---|
| CE17-1 | DMCMal-2 | DTT | 60:60 | 82.3 | 4 | 4.7 |
| C17-2 | DMCMal-2 | PEG-SH-2 | 60:60 | 82.3 | 4 | 30 |
| C17-3 | DMCMal-4 | PEG-SH-2 | 43:43 | 120 | 4 | 21.5 |

Example C18: Young Modulus of Hydrogels Cross-Linked with EDC/NHS or DTT, Comparative Examples, or PEG-SH A circular hydrogel piece as described in examples CE16 and C17 was introduced in a flat glass crystallizer and immersed in PBS. The uniaxial compression was done in PBS at 20-25° C. by using axial force sensor of an universal mechanical tester apparatus (Zwickroell) equipped with a flat compression plate, at a speed of 0.2 mm/min. Initial thickness of the sample was determined from the contact of the plate with the hydrogel, when the force starts to increase. The deformation was defined by the ratio of the compression displacement (mm) and the initial thickness (mm). The Young modulus was determined from the slope of the true strain/deformation curve. The true strain (kPa) corresponds to the ratio of the force (N) to the instantaneous surface area (mm$^2$) of the sample under compression.

TABLE 18

Compression Young modulus of hydrogels

| Example | Polysaccharide type | Polysaccharide (mg/mL) | Cross-linker | Mal: SH (mM:mM) | Number of Samples | Young modulus (kPa) | SD |
|---|---|---|---|---|---|---|---|
| CE16-1 | DMC-3 | 120 | EDC/NHS | — | 3 | 1.9 | 0.2 |
| CE17-1 | DMCMal-2 | 82.3 | DTT | 60:60 | 4 | 2.8 | 0.8 |
| C17-2 | DMCMal-2 | 82.3 | PEG-SH-2 | 60:60 | 3 | 125 | 13 |
| C17-3 | DMC-Mal-4 | 120 | PEG-SH-2 | 43:43 | 2 | 54 | 17 |

Carboxymethyl dextran-based hydrogel cross-linked with EDC/NHS or Carboxymethyl dextran Maleimide-based hydrogel cross-linked with DTT show smaller Young modulus values than hydrogels based on Carboxymethyl dextran Maleimide based cross-linked with PEG-SH. As the Young modulus represents stiffness of the materials, it means that PEG linkers lead to stiffer hydrogels, which were more appropriate to allow surgical implantation.

Example C19: Preparation of Solutions of Concentrated Polysaccharide DextranMal A3

A concentrated polysaccharide solution was prepared by adding an appropriate volume of phosphate buffer 500 mM at pH 4 to sterile freeze-dried polysaccharide described in comparative example A3.

The solution was placed on an orbital shaker 1 h for complete solubilization and stored at 20-25° C. until use for gel preparation the same day.

Comparative Example CE20: Preparation of Hydrogel from DextranMal A3

The preparation of the hydrogel was made in an aseptic environment.

Polysaccharide DextranMal A3 and PEG-SH concentrated sterile solutions prepared according to example C19 and C2 respectively were equilibrated at room temperature (20-25° C.).

45 μL of a concentrated solution of PEG-SH was added to 133 μL of a concentrated solution of polysaccharide DextranMal and 21 μL of phosphate buffer 500 mM at pH 4 in a 2 mL Eppendorf. The solutions were mixed with a pipette and 200 μL of mixture were introduced in a rectangular silicone mould (IBIDI 12×7.75 mm). Gelation was carried out for 1 h at room temperature (20-25° C.). The hydrogel was unmoulded and introduced in a 10 mL PBS (phosphate buffer saline) solution at pH 7.4 for one night. PBS buffer was then renewed, and the hydrogel piece was then stored 4° C. until being used.

TABLE 19

DextranMal A3 based hydrogel

| Example | Polysaccharide DextranMal | PEG-SH | Mal: SH (mM:mM) | [Dextran-Mal] (mg/mL) | pH | [PEG-SH] (mg/mL) | Mixing Temperature (° C.) |
|---|---|---|---|---|---|---|---|
| CE20-1 | DextranMal A3 | PEG-SH-1 | 20:20 | 87 | 4 | 38.4 | 20-25 |

Example C21: Determination of Hydrogel Transparence

Hydrogel's compositions described in examples C4 and C4A and other hydrogels disclosed in Examples C are visually transparent, similarly to water or PBS media.

To quantify the transparency property of the hydrogels, UV absorbance measurements (Jasco® UV spectrophotometer V530) were done by casting hydrogel in a UV cuvette of 10 mm pathlength (Brandt®) and measuring absorbance at 500 nm in comparison to European pharmacopeia standards (StablCal Formazine Reference Suspension, supplied by HACH®). Absorbance measurement at 500 nm is used to quantify the turbidity level of the samples. The samples in the table below were also visually inspected in standardized conditions in front of black panel with a light level between 2,000 and 3,750 Lux (Adelphi® Apollo II Liquid Inspection Unit).

Hydrogel of composition C4A-1 was prepared similarly to example C3A. Polysaccharide DMCMal and PEG-SH concentrated sterile solutions prepared according to example C1 and example C2, respectively, were adjusted with a concentrated NaCl solution in order to obtain isotonic stock solutions (300 mOsm/kg) and equilibrated at 4° C.

250 μL of a concentrated solution of PEG-SH was added to 250 μL of a concentrated solution of polysaccharide DMCMal or DMCVS in a 2 mL Eppendorf. The solutions were mixed with a pipette and a controlled volume of the mixture (400 μL) was introduced the UV cuvette.

Gelation was carried out for 1 h at room temperature (20-25° C.). After one hour, visual inspection and UV absorbance measurement where done and 1.2 mL PBS was added to the UV cuvette. After 1 hour swelling at 37° C. UV measurement and visual inspection where repeated.

TABLE 20

Determination of hydrogel transparency (NTU: Nephelometric Turbidity Unit)

| Example | Composition | Polysaccharide DMCMal | PEG-SH | Mal SH (mM:mM) | Gelation pH | Swelling in PBS | UV Absorbance (Abs. units) | Visual Aspect (at 1 and 2 h for hydrogels) |
|---|---|---|---|---|---|---|---|---|
| C21-1 | C4A-1 | DMCMal-5 | PEG-SH-4 | 10:10 | 4 | No | <0.06 | Transparent |
| C21-2 | C4A-1 | DMCMal-5 | PEG-SH-4 | 10:10 | 4 | Yes | <0.06 | Transparent |
| C21-3 | PBS | — | — | — | — | — | <0.06 | Transparent |
| C21-4 | Std 2 (6 NTU) | — | — | — | — | — | <0.06 | Transparent |
| C21-5 | Std 3 (18 NTU) | — | — | — | — | — | >0.08 | Slightly Turbid |
| C21-6 | Std 4 (30 NTU) | — | — | — | — | — | >1 | Turbid |

These results show that hydrogels according to the invention are transparent.

Part D—Biological Evaluations of Hydrogels

Example D1: Evaluation of Hydrogel Cytotoxicity Profile by Extract Test

The cytotoxicity profile of the hydrogel was evaluated using the extraction method following *ISO 10993-5: Biological evaluation of medical devices* recommendations.

The hydrogels were placed in culture medium (MEM supplemented with 10% Fetal Bovine Serum and 1% Penicilin/Streptomycin) at 3 cm$^2$/ml in a 24-well plate. They were incubated for 24 h at 37° C. and 5% $CO_2$ under orbital agitation (70 rpm) to obtain the hydrogel extraction medium. In parallel, HDFa cells were put at 7500 cells/well in culture medium in 96-well plates and incubated overnight at 37° C. and 5% $CO_2$. The next day, the medium of the cells was removed and replaced with the hydrogel incubation medium. After 24 h of incubation at 37° C. and 5% $CO_2$ of the HDFa cells with the extraction medium, the viability was measured by quantification of the intra-cellular ATP concentration with the ATPLite kit (Perkin Elmer), following the instruction of the manufacturer.

The viability percentage was calculated using the following formula:

$$\text{Viability} = \frac{\text{Signal}_{test\ item}}{\text{Signal}_{control}}$$

The cytotoxicity of hydrogel compositions C4-2, C4-4, C4-9, C4-10, C4A-1 and C4A-2 was evaluated by this extract test. The results are shown in the Table 20 below. The viability percentage was compared to untreated control. The standard deviations (S.D.) of the mean viability of the triplicate wells was calculated (n=2 Hydrogels, each extraction was deposited in triplicate cell wells).

TABLE 20

| Viability of hydrogel by extract test (ISO 10993-5). | | | | | | | | | | | |
|---|---|---|---|---|---|---|---|---|---|---|---|
| | C4-2 | | C4-4 | | C4-9 | | C4-10 | | C4A-1 | | C4A-2 | |
| | Mean | S.D. | Mean | S.D. | Mean | S.D. | Mean | S.D. | Mean | S.D. | Mean | S.D. |
| Viability | 98.5% | 1.5% | 92.4% | 8.8% | 94.4% | 4.1% | 91.3% | 7.8% | 102.2% | 3.0% | 101.3% | 4.0% |

None of the extraction medium showed any cytotoxicity compared to untreated controls (see Table 20). The variation of the length of the DMCMal polymer, the nature of the reactive group ie maleimide or vinylsulfone, the variation of the length of the PEG-SH polymer, the concentration in thiol and maleimide or vinylsulfone reactive groups, as well as the type of cross-linking chemistry does not influence the in vitro biocompatibility of the hydrogels. In conclusion, according to this protocol, hydrogels did not present any in vitro cytotoxicity.

Example D2: In Vitro Viability and Basal Secretion of Encapsulated Pseudo Islets a) Viability of Encapsulated Pseudoislets The encapsulated pseudo islets prepared according to example C9-1 were stained with a Live/Dead staining (ThermoFisher) by supplementing the culture medium with 1 µM calcein-AM and 8 µM ethidium bromide for 30 min. After a washing step, pseudo islets were then imaged using epifluorescence microscopy with a 5× magnification.

The viability score was calculated using the following formula:

$$1 - \frac{\text{Area}_{red}}{\text{Area}_{green}}.$$

The results obtained for viability of encapsulated pseudo islets from D+1 to D+10 are shown in Table 21.

TABLE 21

| Viability assessment of encapsulated pseudo islets in Example C9-1 hydrogel using Live/Dead staining. | | | | |
|---|---|---|---|---|
| Day after encapsulation (D) | D + 1 | D + 2 | D + 3 | D + 10 |
| Viability (%) (±standard deviation) | 95% ± 7% | 97% ± 2% | 92% ± 9% | 96% ± 3% |

After 10 days of encapsulation, more than 90% of pseudo islets were still viable (Table 21).

b) Basal Insulin Secretion Quantification

The basal insulin secretion was measured in the culture medium at different time points and quantified with a sandwich Enzyme Linked ImmunoSorbent Assay (ELISA) for insulin quantification using two monoclonal antibodies. The results were normalized by the basal insulin secretion of naked islets before encapsulation.

The results obtained for the basal insulin secretion of encapsulated pseudo islets from D+3 to D+10 are shown in Table 22.

TABLE 22

| Basal insulin secretion of pseudo islets encapsulated in example C9-1 hydrogel | | | |
|---|---|---|---|
| Day after encapsulation (D) | D + 3 | D + 7 | D + 10 |
| Normalized basal insulin secretion (%) | 90% | 75% | 68% |

These results show that basal insulin secretion of cells was maintained (Table 22).

Together, these results demonstrate that encapsulated pseudo islets survive with no major modification of their basal physiology for at least 10 days after encapsulation.

Example D3: In Vitro Functionality of Encapsulated Pseudo Islets a) Pseudo Islets Encapsulation Pseudo islets were encapsulated as described in Examples C9-2, C9-3 and C9-4.

b) Glucose Stimulated Insulin Secretion 3 days after encapsulation, encapsulated and unencapsulated pseudo islets were washed and incubated 60 min in Krebs buffer containing 0.1% BSA and 1 mM of glucose (low glucose Krebs, equilibration step). Following 3 washing steps, pseudo islets were re-incubated 60 min in low glucose Krebs. Then, the supernatant was collected for insulin content quantification. Encapsulated and unencapsulated pseudo islets were then incubated in Krebs buffer containing 0.1% BSA and 16.6 mM of glucose for 60 min.

Finally, the supernatant was collected for insulin content quantification. Insulin quantification was performed using the ELISA assay described in Example D2b. The secretion index was calculated by dividing the insulin concentration measured in the high glucose Krebs and the low glucose Krebs conditions. The results obtained are shown in Table 23.

S.D stands for standard deviation (n=2 hydrogels).

TABLE 23

Secretion index of unencapsulated and encapsulated pseudo islets.

| Group | Secretion index ± S.D. |
|---|---|
| Unencapsulated pseud oislets | 3.0 ± 0.3 |
| Example C9-2 | 2.6 ± 0.3 |
| Example C9-3 | 2.4 ± 0.5 |
| Example C9-4 | 2.1 ± 0.6 |

The insulin secretion response was similar for encapsulated and unencapsulated pseudo islets (Kruskal-Wallis test, p=0.27) for all tested hydrogel compositions (Table 23), demonstrating therefore that pseudo islet functionality was maintained in hydrogels at least 3 days after encapsulation.

Example D4: Encapsulation does not Affect the Viability and the Functionality of Pseudo Islets In Vitro a) Pseudo Islet and Primary Islet Encapsulation Min-6 pseudo islets were encapsulated as described in Examples C15-1 and C15-2 and maintained in culture medium (see Example B1) in 37° C./5% CO2 incubator. Their viability and functionality were evaluated 3 or 4 days after encapsulation and compared to naked pseudo islets from the same batch.

Primary human islets were encapsulated as described in Examples C15-4, C15-5, C15-7, and C15-9, and maintained in culture medium (Medium 1 from Example B2) in 37° C./5% CO2 incubator. Their viability and functionality were evaluated 1, 2, 6, or 7 days after encapsulation and compared to naked islets from the same batch.

b) Viability Evaluation

Live/Dead staining (ThermoFisher) was used on encapsulated or naked islets or pseudo islets to determine their viability. The protocol was slightly updated compared to example D2a to improve robustness of the method. Phosphate Buffer Saline (PBS) was used to wash the samples. They were then incubated in PBS supplemented with 2 µM calcein-AM and 8 µM ethidium bromide and incubated for 60 min. They were finally washed in PBS and imaged using epifluorescence microscopy.

Quantification of the viability was performed by segmenting the images. The integrated intensity (sum of area pixel intensity) in the green channel, V (live cells), and the integrated intensity in the red channel, D (dead cells), were calculated.

$$\frac{V}{(V+D)}.$$

A viability ratio was obtained by calculating c) Functionality Evaluation Methods To evaluate the functionality of islets or pseudo islets (naked or encapsulated), a perifusion experiment was performed. 1, 2, 6, or 7 days after encapsulation, 400 IEQs (see Example B4) from the batch used for encapsulation (primary islets or pseudo islets) were introduced in a perifusion chamber, as well as encapsulated samples. Chambers were then simulataneously perfused following one of the protocols described in Table 24.

TABLE 24

| Perifusion conditions | | | | |
|---|---|---|---|---|
| Step | Solution | Duration (min) | Flow Collection Frequency | Samples |
| Device: Peri4, Biorep | | | | |
| Equilibration-G3 | Krebs buffer + 3 mM Glucose (G3) | 50 | 100 µL/min No collection | Simplicate |
| 1$^{st}$ Basal secretion-G3 | | 14 | 100 µL/min 1 | |
| Stimulation-G17 | Krebs buffer + 17 mM Glucose (G17) | 38 | well/2 min | |
| 2$^{nd}$ Basal secretion-G3 | Krebs buffer + 3 mM Glucose (G3) | 18 | | |
| Stimulation-KCl | Krebs buffer + 25 mM KCl | 6 | | |
| 3$^{rd}$ Basal secretion-G3 | Krebs buffer + 3 mM Glucose (G3) | 8 | | |
| Device: Custom device | | | | |
| Equilibration-G3 | Krebs buffer + 3 mM Glucose (G3) | 50 | 1 mL/min No collection | Duplicate |
| 1$^{st}$ Basal secretion-G3 | | 10 | 1 mL/min 1 | |
| Stimulation-G15 | Krebs buffer + 15 mM Glucose (G15) | 40 | well/2 min | |
| 2$^{nd}$ Basal secretion-G3 | Krebs buffer + 3 mM Glucose (G3) | 20 | | |

Flow-through buffer was collected and insulin was quantified with an ELISA for insulin quantification.

The Signal fold-increase was calculated by normalizing the insulin concentration measured at each time point by the average insulin concentration measured during the 1$^{st}$ basal secretion step.

The Secretion Index for each sample was calculated as the ratio of the average insulin concentration measured during the stimulation step over the average insulin concentration measured during the 1$^{st}$ basal secretion step.

d) Comparison of the In Vitro Functionality of Naked and Encapsulated Primary Human Islets after 7 Days in Culture Naked and encapsulated primary human islets were evaluated in perifusion 7 days after encapsulation (see FIG. 1): naked islets are represented by circles, encapsulated primary human islets C15-4 are represented by squares and C15-5 are represented by triangle.

1 The results, shown on FIG. 1, show an increased insulin secretion within 10 minutes after the initiation of glucose stimulation in naked islets as well as in encapsulated samples. Following glucose decrease to basal level, insulin secretion returns to basal level. These results strongly suggests that encapsulated islets display similar in vitro functionality to naked islets up to 7 days after encapsulation.

e) Comparison of the In Vitro Viability and Functionality of Naked and Encapsulated Primary Human Islets after 7 Days in Culture Naked primary human islets or Min-6 pseudo islets were evaluated in perifusion and compared to encapsulated samples C15-1, C15-2, C15-4, C15-5, C15-7, and C15-9 using the method described in Example D4c (Device: Custom Device). For these compositions, viability was also assessed as described in Example D4b.

See Table 25. S.D. represents Standard Deviation. N represents le number of experiments and n the number of independent samples per experiment. N.D. means not determined.

TABLE 25

Viability and functionality results of naked pseudo islets or islets compared to encapsulated samples.

| Cell Type | Encapsulation duration (days) | Sample | Viability ± S.D. | Functionality ± S.D. (perifusion secretion index) | N/n |
|---|---|---|---|---|---|
| Min-6 | 3 and 4 | Naked pseudoislets | 93% ± 9% | 3.6 ± 1.3 | N = 2/ n = 2 |
|  |  | C15-2 | 71% ± 2% | 5.3 ± 2.3 |  |
|  |  | C15-1 | 82% | 3.7 | N = 1/ n = 1 |
| Primary human islets | 1 | Naked islets | N.D. | 2.1 |  |
|  |  | C15-4 | N.D. | 2.2 |  |
|  | 2 | Naked islets | 91% ± 6% | 2.1 |  |
|  |  | C15-9 | 81% ± 10% | 1.8 |  |
|  | 6 | Naked islets | 75% ± 10% | 2.0 |  |
|  |  | C15-5 | 87% ± 6% | 1.9 |  |
|  | 7 | Naked islets | 89% ± 7% | 1.9 |  |
|  |  | C15-7 | 87% ± 4% | 1.9 |  |
|  |  | C15-9 | 90% ± 0% | 1.4 |  |

The results show a 11-22% decrease in Min-6 encapsulated pseudo islets viability compared to naked pseudo islets, and no significant difference in secretion index, suggesting similar functionality 3 to 4 days after encapsulation (Welch's test, p=0.17).

No difference neither in viability nor in functionality for encapsulated primary human islets compared to naked islets up to 7 days after encapsulation was observed. C15-9 sample 7 days after encapsulation shows a slightly lower functionality compared to naked islets that could be simply due to sample variability.

These results strongly suggest that encapsulation does not significantly impact the viability (ANOVA across primary human islet encapsulation conditions, p=0.34) and functionality of encapsulated primary human islets in the hydrogels.

Example D5: Long-Term In Vitro Viability and Functionality of Encapsulated Primary Islets a) Primary Islet Encapsulation Primary rat islets were encapsulated 2 days after isolation, as described in Example C15-3 and maintained in culture medium (RPMI medium supplemented with 10% Foetal Bovine Serum, 2 g/L glucose final concentration and 1% Penicillin/Streptomycin) in 37° C./5% CO2 incubator. Primary human islets were encapsulated as described in Example C15-8 and maintained in culture medium (Medium 2 from Example B2) in 37° C./5% CO2 incubator.

The primary rat islets functionality was evaluated 1, 5, 8, 15 and 22 days after encapsulation. The primary human islet functionality was evaluated 3, 7, 10, 14, and 21 days after encapsulation. Each time point was evaluated with n=2 hydrogels, using the method described in Example D4c (Device: Peri4, Biorep). See Table 26. N.D. means Not Determined. S.D. means Standard Deviation

TABLE 26

Long-term in vitro viability and functionality of encapsulated primary islets.

|  | Encapsulation duration (days) | Sample | Viability (%) ± S.D. | Functionality ± S.D. (perifusion secretion index) |
|---|---|---|---|---|
| Primary Rat Islets | 1 | C15-3 | 63% ± 7% | 3.8 ± 0.0 |
|  | 5 |  | N.D. | 5.6 ± 2.2 |
|  | 8 |  | 83% ± 9% | 2.0 ± 1.3 |
|  | 15 |  | 68% ± 10% | 3.8 ± 2.0 |
|  | 22 |  | N.D. | 3.1 ± 1.3 |
| Primary Human Islets | 3 | C15-8 | 86% ± 5 % | 3.0 ± 0.2 |
|  | 7 |  | 79% ± 1% | 3.2 ± 0.5 |
|  | 10 |  | N.D. | 2.9 ± 0.5 |
|  | 14 |  | 63% ± 6% | 2.8 ± 0.5 |
|  | 21 |  | 75% ± 15% | 4.3 ± 1.6 |

N = 1 independent experiment, n = 2 samples

Results show that the viability of the encapsulated primary rat islets was maintained in vitro until at least 15 days after encapsulation (ANOVA, p=0.65). Similarly, primary human islets viability was maintained in vitro at least 21 days after encapsulation (ANOVA, p=0.19).

Results show that the perifusion secretion index of the encapsulated primary rat islets was stable and maintained above 2 until at least 22 days after encapsulation (ANOVA, p=0.35), showing that the encapsulated primary rat islets were functional. Similar results were observed on primary human islets until at least 21 days after encapsulation (ANOVA, p=0.44).

Altogether, these results show that the in vitro viability and functionality of encapsulated primary rat islets (C15-3), were maintained over time after encapsulation, for at least 15 days and 22 days, respectively. Moreover, the viability and functionality of encapsulated primary human islets (C15-8) were maintained in vitro for at least 21 days.

Example D6: In Vivo Survival and Functionality of Encapsulated Islets Xenotransplanted in Rat Omentum a) Primary Human Islet Encapsulation Primary human islets were encapsulated as described in example C15-6 and implanted in rat omentum for 3 and 6 days.

In Vivo Implantation

Wistar rats weighing between 250 and 400 g were used. Anesthesia was performed with isoflurane.

Each animal was placed in the supine position on a warmed pad. The fur was shaved from surgical area with a surgical blade. The surgical site was disinfected with povidone iodine solution.

A 2-3 cm long midline incision was made in the abdomen. The intestines were moved to the left side and covered with saline-soaked gauze to prevent dehydration. The stomach was fully exposed, and the omentum was spread on a humid gauze. Two implants were placed onto the omentum and covered with it (wrapping technique). Non-resorbable suture stitches (Prolene 6/0) were made on the omentum to maintain the implants in place and avoid their slippage and/or overlapping. Prior to closing the abdomen, 2 mL of physiological saline solution were dispensed into the abdominal cavity to prevent dehydration. The peritoneum with muscular layer was closed with continuous non-resorbable suture (Prolene 4/0), then the skin was sutured (Prolene 4/0) by interrupted single stitches and the incision cleaned with povidone iodine solution.

After surgery, each animal was moved to a recovery area and monitored for recovery from anesthesia until sternal recumbency was achieved. After recovery, the animals were group-housed and observed for general health.

At the designated time points, the animals were sacrificed. The implantation sites were collected and one explant from each animal was dissected free from tissues for post-implantation perifusion and viability assays. Blood was collected by exsanguination at the aortic bifurcation level.

b) Explant Evaluation

Explants viability and functionality were evaluated as described in examples D4b and D4c (Device: Peri4, Biorep), 3 and 6 days after in vivo implantation. See Table 27. S.D. represents Standard Deviation.

TABLE 27

Functionality of encapsulated primary human islet explants after in vivo implantation in rat omentum.

| Implantation duration (days) | Sample | Viability ± S.D. | Functionality (perifusion secretion index) |
|---|---|---|---|
| 3 | C15-6 | 78 ± 15% | 1.7 ± 0.8 |
| 6 | | 77 ± 19% | 1.8 ± 0.2 |

N = 1 independent experiment, n = 1 sample.

The results show that the encapsulated islets had viability above 75% and insulin increase in response to glucose at least 6 days after in vivo implantation in omentum.

Example D7: In Vivo Short-Term Local Tolerance of Hydrogels: DMC-PEG Versus Dextran-PEG Local tolerance of hydrogels was evaluated based on guideline ISO 10993 Part 6 (2016): Tests for local effects after implantation.

C4-2, C4-3 (both DMC-PEG) and CE20-1 (Dextran-PEG) hydrogels were implanted in the dorsal subcutaneous tissue of rabbits for 1 week. The local tissue effects as well as the aspect of hydrogels were evaluated macroscopically and by histopathologic analysis (n=5 sites per article and per time-period) as recommended by ISO 10993 Part 6 as follows: after sacrifice of the animals and explanation of the hydrogels, tissue reactivity produced by the implants was evaluated by scoring its various components on a 0 to 4 scale. The components evaluated were polymorphonuclear cells, lymphocytes, plasma cells, macrophages, giant cells, necrosis on one part, and neovascularization, fibrosis and fatty infiltrate on a second part. The various inflammatory cell types or morphologic features were only reported if present. The average score obtained for each test article, minus the average score obtained by the negative control article HDPE (high density polyethylene; as recommended by ISO 10993 Part 6), gives a tissue reactivity score.

Macroscopically, C4-2 and C4-3 hydrogels were well preserved in shape, size, color and consistency. On the contrary, CE20-1 hydrogels were larger than the implanted material. In addition, CE20-1 induced a stronger tissue reaction (diffuse redness) compared to C4-2 and C4-3.

After histopathology examination, and according to the scoring scale for tissue reactivity from the guideline ISO10993 Part 6, C4-2 and C4-3 were found to induce "minimal to no reaction", whereas CE20-1 was graded as inducing a "moderate reaction".

TABLE 28

Scoring and tissue reactivity for C4-2, C4-3 and CE20-1 versus the negative control (NC) HDPE after 1 week of subcutaneous implantation in the rabbit.

| Average score | C4-2 | C4-3 | CE20-1 | HDPE (NC) |
|---|---|---|---|---|
| F1. Inflammation (x2) | 30 | 24 | 42 | 36 |
| F2. Neovascularization | 3 | 6 | 7 | 2 |
| Fibrosis | 4 | 3 | 10 | 6 |
| Fatty infiltrate | 0 | 0 | 0 | 0 |
| Ave | 7.4 | 6.6 | 20.2 | 8.8 |
| Reaction score vs HDPE | 0 | 0 | 11.4 | n/a |
| Tissue reactivity | No | No | Moderate | n/a | n/a: not applicable.

These results show that hydrogels formed using DMC present a better tolerance than those forms using Dextran.

Example D8: In Vivo Long-Term Local Tolerance of Hydrogels

Local tolerance of hydrogels was evaluated based on the guideline ISO10993 Part 6 (2016): Tests for local effects after implantation.

C4A-1 and C4A-2 hydrogels and a disc-shaped HDPE of the same size as the disc-shaped hydrogel were implanted in the dorsal subcutaneous tissue of rats for 13 weeks. The local tissue effects as well as the aspects of hydrogels were evaluated macroscopically and by histopathologic analysis (n=5 sites per article and per time-period) as described in Example D7.

Macroscopically, C4A-1 and C4A-2 hydrogels were well preserved in shape, size, color and consistency. In addition, tissue reaction (redness) was rarely observed.

After histopathology examination, and according to the scoring scale for tissue reactivity from guideline ISO10993 Part 6, C4A-1 and C4A-2 were found to induce "minimal to no reaction", and with an average score reaction score inferior to the negative control HDPE.

TABLE 29

Scoring and tissue reactivity for C4A-1 and C4A-2 hydrogels versus the negative control (NC) HDPE after 13 weeks of subcutaneous implantation in the rat.

| Average score | C4A-1 | C4A-2 | HDPE (NC) |
|---|---|---|---|
| F1. Inflammation (x2) | 18 | 18 | 22 |
| F2. Neovascularization | 6 | 4 | 5 |
| Fibrosis | 8 | 9 | 12 |
| Fatty infiltrate | 0 | 0 | 0 |
| Ave | 6.4 | 7.8 | 11.2 |
| Reaction score vs HDPE | 0 | 0 | n/a |
| Tissue reactivity | No | No | n/a | n/a: not applicable.
Therefore, both hydrogels show an excellent local tolerance after 13 weeks of implantation in the subcutis of the rat.

Example D9: In Vivo Immuno-Isolation Properties of Hydrogels

Immuno-isolation properties of hydrogels were assessed during the course of studies involving implantation of either xenogenic (human in the mouse) or allogenic (rat in the rat) encapsulated islets of Langerhans in the omentum or in the dorsal subcutaneous tissue. Mice and rats were immuno-competent.

a) Xenograft

Swiss mice weighing between 25-35 g were used.

Each animal was implanted with one disc-shaped C15-10 implant containing approximately 1 000 islets' equivalents (IEq) at a density of 33 000 IEq/mL.

Before implantation, each mouse was placed on an inhalant anesthetic (isoflurane) with a mask.

For implantation in the subcutaneous tissue (SC), a local anesthetic ointment (xylocaine) was applied on the surgical area. Each animal was placed in the prone position. For omental implantation, the animal was placed in the supine position. Animals were placed on a warmed pad. A neutral ophthalmic ointment was applied to both eyes to protect the corneas from drying and re-applied as needed. The fur was shaved from surgical area with a surgical blade. The surgical site was disinfected with povidone iodine solution. An incision large enough to accommodate the implant was made through the skin slightly below the interscapular level and perpendicular to the vertebral column. A pocket was formed by blunt dissection of the subcutaneous tissues and the implant was introduced in this compartment. The skin was closed with non-absorbable thread (Prolene 5/0) and surgical glue (3M Vetbond), and the incision cleaned with povidone iodine solution.

For omental implantation, a 2-3 cm long midline incision was made in the abdomen. The intestines were moved to the left side and covered with saline-soaked gauze to prevent dehydration. With the help of cotton swabs, the stomach was fully exposed, and the omentum located and carefully unfolded using a pair of forceps. The stomach was flipped over to expose the retro-gastric cavity. One implant was placed in this cavity and covered with the omentum. The stomach was then propelled back into its original position.

After surgery, each animal was moved to a recovery area and monitored for recovery from the anesthesia until sternal recumbency was achieved. A diet gel was available in the cages (Diet Gel recovery). After recovery, the animals were group-housed and observed for general health.

Animals were sacrificed 26 days after implantation, and implantation sites macroscopically observed before being collected with the implants for histopathology. No macroscopic inflammatory reaction was noted around the implants.

Histopathology examination of encapsulated human islets did not disclose infiltration of inflammatory host cells into the hydrogel and no signs of an inflammatory host response in the tissues surrounding the implants was noted, regardless of the site of implantation. This supports the good tolerance of C15-10 hydrogel and its capacity to immuno-isolate xenogenic islets against the host immune reaction.

b) Allograft

Allograft was performed in diabetic male Wistar rats. Diabetes was induced by intraperitoneal administration of streptozotocin at 45 mg/kg. Animals were implanted 10 weeks after induction. At the time of surgery, animals weighed between 250 and 350 g.

Each animal was implanted with two disc-shaped C15-13 implants containing each approximately 2 300 IEq at a density of 33 000 IEq/mL.

Animals were anesthetized with isoflurane, weighed, and then injected with an anti-inflammatory treatment (Meloxicam, 1 mg/kg SC) and a large spectrum antibiotic (Shotapen 0.1 mL/kg SC). In addition, an anesthetic ointment (xylocaine) was applied on the surgical area. Each rat was placed in supine position on a heated pad and prepared for surgery.

A midline incision was made in the abdomen. The intestines were moved on the left of the cavity with cotton swabs in order to expose the stomach. The omentum was localized and carefully spread on a wet gauze. Using forceps, the omental sheets were separated in order to create a pocket. Two implants were placed in the created space, avoiding superposition, and covered with the omental tissue. The edges of the pocket were sealed with biological glue (Tisseel, Baxter) when needed. Implants were localized with a non-resorbable suture (Mersilk™ 4-0). The stomach and intestines were replaced in the abdominal cavity.

Before suturing the incision, intraperitoneal cavity was rehydrated with NaCl 0.9 solution (10% of blood volume). The abdomen was sutured with resorbable suture (Vicryl™ 4-0).

Right after the surgery, a dietary gel (Diet gel) was placed in individual cages and animals observed until sternal recumbency was achieved. The animals were housed individually until recovery (at least 4 days), then group-house.

After surgery, the animals received the anti-inflammatory treatment (Meloxicam, 1 mg/kg SC) once daily for three consecutive days and two injections of Shotapen (0.1 mL/kg SC) three and six days post-surgery.

Blood was collected on Day 21 for hematobiochemical analyses. The results did not disclose any evidence of an inflammatory reaction related to the implants.

Animals were sacrificed 35 days after surgery and implantation sites macroscopically observed before being collected with the implants for histopathology. No macroscopic sign of inflammation was noted.

Histopathology examination of encapsulated rat islets did not disclose infiltration of inflammatory host cells into the hydrogel, except when the hydrogel was discontinued due to breakage. No sign of an inflammatory host response in the tissues surrounding the implants was noted, regardless of the site of implantation. This supports the good tolerance of C15-13 hydrogel and its capacity to immuno-isolate allogenic islets against the host immune reaction.

Example D10: In Vivo Proof of Functionality of Encapsulated Islets

In vivo functionality of encapsulated human islets was evaluated in rats implanted in the omentum with two disc-shaped C15-12 implants containing human islets. Each animal was implanted with 5 000 IEq at the density of 38 000 IEq/mL.

Omental implantation was performed as described in Example D9.

Islets' functionality was assessed by measurement of human C-peptide in the serum up to 6 days after implantation. Blood was collected every 2-3 days, 15-20 minutes after administration of glucose to stimulate insulin secretion. Glucose stimulation was performed by administration of 2 g/kg glucose by intraperitoneal route. Plasma was prepared and C-peptide measured using a specific ELISA immunoassay (Mercodia, Ref. 10.1141.01).

C-peptide plasma levels were detectable for all animals at 3 and 6 days post implantation, indicating that encapsulated islets were functional and that the hydrogel allowed diffusion of insulin into the bloodstream.

Example D11: In Vivo Proof of Efficacy of Encapsulated Islets

In vivo efficacy of encapsulated human islets was evaluated in diabetic rats. Diabetes was induced as described in Example D7. Efficacy was assessed by the ability of islets to regulate hyperglycemia, measured by the monitoring of blood glucose.

Each animal was implanted with two disc shaped C15-13 implants, as described in Example D9b. Omental implantation of encapsulated islets was performed as described in Example D9b. As control, naked islets were implanted in another group of animals as follows: few drops of a biological glue (Tisseel, Baxter) were applied on the omentum and let to polymerize. Once the glue has polymerized, the required number of islets was injected in the glue.

Four hours before blood glucose measurement, animals were deprived of food to minimize variability in blood glucose. Blood glucose was measured prior to implantation (basal value, e.g., on Day 0), on Day 14. One drop of blood was collected from the cut tail tip and blood glucose measured using a One Touch® glucose-meter (from Lifescan).

Blood glucose levels were above the detection limit of 600 mg/dL in all diabetic rats before implantation. Glycemia of control rats remained above 600 mg/dL at Day 14, while glycemia decreased in all rats implanted with C15-13 implants, reaching a mean value of 340 mg/dL (individual glycemia values between 252 and 422 mg/dL) 14 days after implantation.

TABLE 30

Day 1 and Day 14 individual and mean blood glucose levels (in mg/dL) measured in diabetic rats implanted in the omentum with naked islets or C15-13 implants.

| Implants | Rat ID | Pre-implantation | D14 |
|---|---|---|---|
| Naked Islets | 1 | 600 | 600 |
| | 2 | 600 | 600 |
| | 3 | 600 | 600 |
| | Mean | 600 | 600 |
| C15-13 | 4 | 600 | 422 |
| | 5 | 600 | 252 |
| | 6 | 600 | 326 |
| | 7 | 600 | 354 |
| | Mean | 600 | 340 |

Naked islets were not able to control hyperglycemia, strongly suggesting that they were not functional, possibly due to host reaction. On the contrary, encapsulated islets (C15-13) led to a very strong reduction in glycemia 14 days after implantation, indicating that encapsulated islets were viable and functional, thanks to the ability of the hydrogel to provide immune-isolation while preserving their efficacy.

The invention claimed is:

1. Cross-linked dextran polymer, bearing carboxylate groups, wherein at least two saccharidic units of dextran belonging to two different polymer chains are covalently linked by at least one at least divalent radical $L(-)_i$, wherein the at least one at least divalent radical $L(-)_i$ is covalently bound to the dextran polymer backbone with i —$(R_1)_m G_1$-_ radical, wherein, $L(-)_i$ is a linear or branched polyether bearing at its ends, heteroatoms, i is the valence of L and is an integer comprised from 2 to 8 ($2 \leq i \leq 8$) wherein i=2 and $L(-)_i$ is a radical issued from a mercaptopolyethyleneglycol according to formula II:

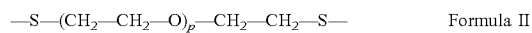
—S—(CH$_2$—CH$_2$—O)$_p$—CH$_2$—CH$_2$—S—     Formula II wherein p is an integer comprised from 8 to 1000 ($8 \leq p \leq 1000$), or $L(-)_i$ is a branched polyether bearing at its ends, heteroatoms comprising at most 8 arms, m is an integer equal to 0 or 1, —$R_1$— is a linear or branched alkyl divalent radical comprising from 1 to 6 carbon atoms and optionally heteroatoms, -$G_1$- is a linear or branched or cyclic alkyl divalent radical comprising from 1 to 6 carbon atoms and may comprise heteroatoms.

2. Cross-linked dextran polymer according to claim 1, wherein the carboxylate groups bound to the saccharidic units are bound by ether bonds and chosen amongst carboxylate groups according to formula I

—(CH$_2$)$_n$—COX     Formula I wherein n is an integer comprised from 1 to 7 ($1 \leq n \leq 7$), and X is chosen amongst —OH, —ONa, —OK or —$(R_1)_m G_1$- radical.

3. Crosslinked dextran polymer according to claim 1, wherein $L(-)_i$ is a linear polyether radical bearing at its ends 2 sulfur atoms.

4. Crosslinked dextran polymer according to claim 1 wherein $L(-)_i$ is a radical according to formula III issued from a mercaptoethyl polyoxyethylene:

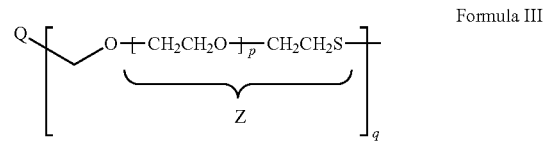
Formula III wherein Q is either a carbon atom or an alkyl chain comprising from 1 to 10 carbon atoms, the alkyl chain may comprise heteroatom chosen from the group consisting of oxygen, sulfur and nitrogen p is an integer comprised from 8 to 1000 ($8 \leq p \leq 1000$), q is an integer comprised from 2 to 8 ($2 \leq q \leq 8$), and Z is —(CH$_2$—CH$_2$O)$_p$—CH$_2$—CH$_2$—S—.

5. Cross-linked polymer according to claim 1, wherein —$R_1$— is a linear or branched alkyl divalent radical comprising from 1 to 6 carbon atoms and optionally heteroatoms.

6. Cross-linked dextran polymer according to claim 1, wherein the radical —$R_1$— is covalently bound by an amide function resulting of the reaction of a carboxylate group borne by the dextran with one —$R_1$— precursor or —$(R_1)_m$-$G_1$- precursor bearing an amine function.

7. Cross-linked dextran polymer according to claim 1, wherein radical —$R_1$— is covalently bound by an ether function resulting of the reaction of a hydroxyl function borne by the dextran with one —$R_1$— precursor or —$(R_1)_m$-$G_1$- precursor bearing a leaving group.

8. Cross-linked dextran polymer according to claim 1, wherein -$G_2$, the precursor of radical -$G_1$-, is chosen amongst maleimide or vinylsulfone or a group comprising a maleimide or a vinylsulfone.

9. Cross-linked dextran polymer according to claim 1 wherein the dextran polymer backbone is according to formula XII,

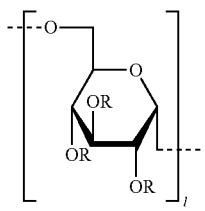

Formula XII wherein R is chosen among——H, —$(CH_2)_n$—COX or —$(R_1)_m G_1$-; n, m, X, —$R_1$—, -$G_1$- and $L(-)_i$ wherein $L(-)_i$ is a linear or branched polyether bearing at its ends, heteroatoms,
i is the valence of L and is an integer comprised from 2 to 8 ($2 \leq i \leq 8$),
wherein
i=2 and $L(-)_i$ is a radical issued from a mercaptopolyethyleneglycol according to formula II:

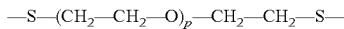  Formula II wherein p is an integer comprised from 8 to 1000 ($8 \leq p \leq 1000$), or -$L(-)_i$ is a branched polyether bearing at its ends, heteroatoms comprising at most 8 arms,
m is an integer equal to 0 or 1,
—$R_1$— is a linear or branched alkyl divalent radical comprising from 1 to 6 carbon atoms and optionally heteroatoms,
-$G_1$- is a linear or branched or cyclic alkyl divalent radical comprising from 1 to 6 carbon atoms and may comprise heteroatoms,
-n is an integer comprised from 1 to 7 ($1 \leq n \leq 7$), and
—X is chosen amongst —OH, —ONa, —OK or —$(R_1)_m G_1$- radical,
and $L(-)_i$ being covalently bound to another dextran polymer backbone with a —$(R_1)_m G_1$-_radical, and
l is comprised from 20 to 5000 ($20 \leq l \leq 5000$).

10. Cross-linked dextran polymer according to claim 1, wherein
the degree of substitution ($DS_1$) of the dextran backbone with the —$(R_1)_m G_1$-groups is comprised in the range from 0.001 to 0.4 ($0.001 \leq DS1 \leq 0.4$) and/or the degree of substitution ($DS_2$) of the dextran backbone with the carboxylate groups according to formula I is comprised in the range from 0.5 to 3 ($0.5 \leq DS_2 \leq 3$) and/or the dextran polymer has a molar ratio (DC) between the molar concentration of the —$(R_1)_m G_1$- radical and the molar concentration of the reactive functions of the crosslinker $L(-)_i$ comprised in a range from 0.5 to 1.5 ($0.5 \leq DC \leq 1.5$).

11. Crosslinked dextran polymer according to claim 1 wherein $L(-)_i$ is a radical according to formula VII

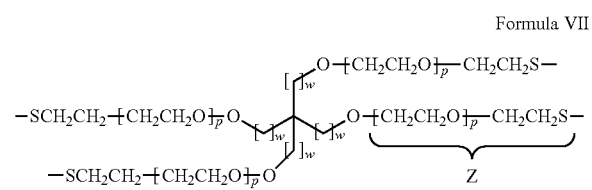

Formula VII wherein
Z is —$(CH_2-CH_2O)_p$—$CH_2$—$CH_2$—S—
p is an integer comprised from 8 to 1000 ($8 \leq p \leq 1000$)
w is an integer comprised from 1 to 2, ($1 \leq w \leq 2$).

12. Crosslinked dextran polymer according to claim 1 wherein $L(-)_i$ is a radical according to formula VII'

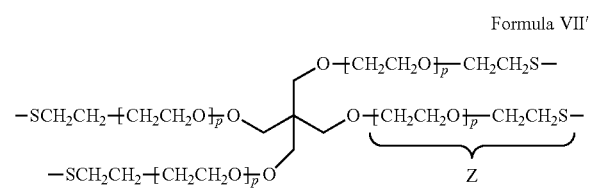

Formula VII' wherein:
p is an integer comprised from 8 to 1000, ($8 \leq p \leq 1000$) and
Z is —$(CH_2-CH_2O)_p$—$CH_2$—$CH_2$—S—.

13. Hydrogel comprising a cross-linked dextran polymer, bearing carboxylate groups, wherein at least two saccharidic units of dextran belonging to two different polymer chains are covalently linked by at least one at least divalent radical $L(-)_i$, wherein the at least one at least divalent radical $L(-)_i$ is covalently bound to the dextran polymer backbone with i —$(R_1)_m G_1$-_radical,
wherein,
$L(-)_i$ is a linear or branched polyether bearing at its ends, heteroatoms,
i is the valence of L and is an integer comprised from 2 to 8 ($2 \leq i \leq 8$)
m is an integer equal to 0 or 1,
—$R_1$— is a linear or branched alkyl divalent radical comprising from 1 to 6 carbon atoms and optionally heteroatoms,
-$G_1$- is a linear or branched or cyclic alkyl divalent radical comprising from 1 to 6 carbon atoms and may comprise heteroatoms.

14. Hydrogel according to claim 13 wherein $L(-)_i$ is a radical according to formula VII

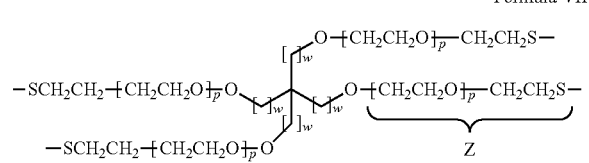

Formula VII wherein $Z$ is $-(CH_2-CH_2O)_p-CH_2-CH_2-S-$ $p$ is an integer comprised from 8 to 1000 ($8 \leq p \leq 1000$)

$w$ is an integer comprised from 1 to 2, ($1 \leq w \leq 2$).

15. Hydrogel according to claim 13 wherein $L(-)_i$ is a radical according to formula VII'

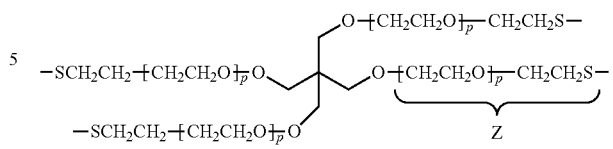

Formula VII'

Wherein:

$p$ is an integer comprised from 8 to 1000, ($8 \leq p \leq 1000$) and $Z$ is $-(CH_2-CH_2O)_p-CH_2-CH_2-S-$.

16. Hydrogel according to claim 13, wherein it further comprises biological cells.

17. Implant comprising the hydrogel according to claim 13.

18. A method for treating a disorder or disease in a mammal wherein the disorder or disease is due to lack or malfunction of endocrine function of pancreas organ, comprising adminstering the hydrogel according to claim 13 to a mammal in need thereof.

* * * * *